US012747260B2

(12) United States Patent
McPherson et al.

(10) Patent No.: US 12,747,260 B2
(45) Date of Patent: Sep. 29, 2026

(54) SYNTHESIS OF OLIGOMERIC COMPOUNDS COMPRISING PHOSPHOROTHIOATE DIESTER AND PHOSPHODIESTER LINKAGES

(71) Applicant: Ionis Pharmaceuticals, Inc., Carlsbad, CA (US)

(72) Inventors: Andrew K. McPherson, San Diego, CA (US); Andrew A. Rodriguez, San Diego, CA (US); Daniel C. Capaldi, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 1059 days.

(21) Appl. No.: 17/611,765

(22) PCT Filed: May 15, 2020

(86) PCT No.: PCT/US2020/033196
§ 371 (c)(1),
(2) Date: Nov. 16, 2021

(87) PCT Pub. No.: WO2020/236618
PCT Pub. Date: Nov. 26, 2020

(65) Prior Publication Data

US 2022/0251128 A1 Aug. 11, 2022

Related U.S. Application Data

(60) Provisional application No. 62/953,087, filed on Dec. 23, 2019, provisional application No. 62/849,799, filed on May 17, 2019.

(51) Int. Cl.

| | |
|---|---|
| ***C07H 1/00*** | (2006.01) |
| ***C07H 21/02*** | (2006.01) |
| ***C07H 21/04*** | (2006.01) |

(52) U.S. Cl.
CPC ............... *C07H 1/00* (2013.01); *C07H 21/02* (2013.01); *C07H 21/04* (2013.01)

(58) Field of Classification Search
CPC ........... C07H 1/00; C07H 21/02; C07H 21/04
See application file for complete search history.

(56) References Cited

U.S. PATENT DOCUMENTS

| | | | |
|---|---|---|---|
| 3,687,808 | A | 8/1972 | Merigan et al. |
| 4,751,219 | A | 6/1988 | Kempen et al. |
| 4,845,205 | A | 7/1989 | Huynh Dinh et al. |
| 5,034,506 | A | 7/1991 | Summerton et al. |
| 5,130,302 | A | 7/1992 | Spielvogel et al. |
| 5,134,066 | A | 7/1992 | Rogers et al. |
| 5,166,315 | A | 11/1992 | Summerton et al. |
| 5,175,273 | A | 12/1992 | Bischofberger et al. |
| 5,185,444 | A | 2/1993 | Summerton et al. |
| 5,367,066 | A | 11/1994 | Urdea et al. |
| 5,432,272 | A | 7/1995 | Benner |
| 5,434,257 | A | 7/1995 | Matteucci et al. |
| 5,457,187 | A | 10/1995 | Gmelner et al. |
| 5,457,191 | A | 10/1995 | Cook et al. |
| 5,459,255 | A | 10/1995 | Cook et al. |
| 5,484,908 | A | 1/1996 | Froehler et al. |
| 5,502,177 | A | 3/1996 | Matteucci et al. |
| 5,525,711 | A | 6/1996 | Hawkins et al. |
| 5,552,540 | A | 9/1996 | Haralambidis |
| 5,587,469 | A | 12/1996 | Cook et al. |
| 5,587,470 | A | 12/1996 | Cook et al. |
| 5,594,121 | A | 1/1997 | Froehler et al. |
| 5,596,091 | A | 1/1997 | Switzer |
| 5,614,617 | A | 3/1997 | Cook et al. |
| 5,645,985 | A | 7/1997 | Froehler et al. |
| 5,681,941 | A | 10/1997 | Cook et al. |
| 5,698,685 | A | 12/1997 | Summerton et al. |
| 5,703,218 | A | 12/1997 | Urdea et al. |
| 5,750,692 | A | 5/1998 | Cook et al. |
| 5,763,588 | A | 6/1998 | Matteucci et al. |
| 5,783,684 | A | 7/1998 | Reddy et al. |
| 5,808,027 | A | 9/1998 | Cook et al. |
| 5,811,534 | A | 9/1998 | Cook et al. |

(Continued)

FOREIGN PATENT DOCUMENTS

| | | |
|---|---|---|
| WO | WO 1997/020563 | 6/1997 |
| WO | WO 1997/046098 | 12/1997 |

(Continued)

OTHER PUBLICATIONS

Bergstrom, D., & Schmaltz, T. Organoiron-mediated alkylation of phosphite esters: synthesis of (dicarbonyl)(.eta.5-cyclopentadienyl)iron-derived nucleoside phosphonate esters. The Journal of Organic Chemistry, 57(3), 873-876. https://doi.org/10.1021/jo00029a017 (Year: 1992).*

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Biessen et al., "Novel hepatotrophic prodrugs of the antiviral nucleoside 9-(2-phosphonylmethoxyethyl)adenine with improved pharmacokinetics and antiviral activity" FASEB J. (2000) 14:1784-1792.

Biessen et al., "Synthesis of Cluster Galactosides with High Affinity for the Hepatic Asialoglycoprotein Receptor" J. Med. Chem. (1995) 38:1538-1546.

(Continued)

*Primary Examiner* — Andrea Olson
*Assistant Examiner* — Hoi Yan Lee
(74) *Attorney, Agent, or Firm* — McNeill PLLC

(57) ABSTRACT

The present disclosure provides methods for synthesizing oligomeric compounds having at least one phosphorothioate diester linkage and at least one phosphate diester internucleoside linkage. In certain embodiments, the present disclosure provides oxidation reagents that produce low amounts of unwanted phosphate diester impurities in oligomeric compounds having at least one phosphorothioate diester linkage and at least one phosphate diester internucleoside linkage.

13 Claims, 2 Drawing Sheets

Specification includes a Sequence Listing.

(56) References Cited

U.S. PATENT DOCUMENTS

| | | | |
|---|---|---|---|
| 5,830,653 | A | 11/1998 | Froehler et al. |
| 5,859,221 | A | 1/1999 | Cook et al. |
| 5,948,903 | A | 9/1999 | Cook et al. |
| 5,994,517 | A | 11/1999 | Ts'o et al. |
| 6,005,087 | A | 12/1999 | Cook et al. |
| 6,005,096 | A | 12/1999 | Matteucci et al. |
| 6,166,199 | A | 12/2000 | Cook et al. |
| 6,268,490 | B1 | 7/2001 | Imanishi et al. |
| 6,300,319 | B1 | 10/2001 | Manoharan |
| 6,383,812 | B1 | 5/2002 | Chen et al. |
| 6,525,031 | B2 | 2/2003 | Manoharan |
| 6,525,191 | B1 | 2/2003 | Ramasamy |
| 6,531,584 | B1 | 3/2003 | Cook et al. |
| 6,620,916 | B1 | 9/2003 | Takahara et al. |
| 6,660,720 | B2 | 12/2003 | Manoharan et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 6,906,182 | B2 | 6/2005 | Ts'o et al. |
| 6,908,903 | B1 | 6/2005 | Theodore et al. |
| 7,034,133 | B2 | 4/2006 | Wengel et al. |
| 7,053,207 | B2 | 5/2006 | Wengel |
| 7,135,565 | B2 | 11/2006 | Dellinger et al. |
| 7,262,177 | B2 | 8/2007 | Ts'o et al. |
| 7,399,845 | B2 | 7/2008 | Seth et al. |
| 7,427,672 | B2 | 9/2008 | Imanishi et al. |
| 7,491,805 | B2 | 2/2009 | Vargeese et al. |
| 7,547,684 | B2 | 6/2009 | Seth et al. |
| 7,569,686 | B1 | 8/2009 | Bhat et al. |
| 7,572,582 | B2 | 8/2009 | Wengel et al. |
| 7,582,744 | B2 | 9/2009 | Manoharan et al. |
| 7,666,854 | B2 | 2/2010 | Seth et al. |
| 7,696,345 | B2 | 4/2010 | Allerson et al. |
| 7,723,509 | B2 | 5/2010 | Manoharan et al. |
| 7,741,457 | B2 | 6/2010 | Swayze et al. |
| 7,750,131 | B2 | 7/2010 | Seth et al. |
| 7,851,615 | B2 | 12/2010 | Manoharan et al. |
| 7,875,733 | B2 | 1/2011 | Bhat et al. |
| 7,939,677 | B2 | 5/2011 | Bhat et al. |
| 8,022,193 | B2 | 9/2011 | Swayze et al. |
| 8,030,467 | B2 | 10/2011 | Seth et al. |
| 8,034,909 | B2 | 10/2011 | Wengel et al. |
| 8,080,644 | B2 | 12/2011 | Wengel et al. |
| 8,088,746 | B2 | 1/2012 | Seth et al. |
| 8,088,904 | B2 | 1/2012 | Swayze et al. |
| 8,106,022 | B2 | 1/2012 | Manoharan et al. |
| 8,124,745 | B2 | 2/2012 | Allerson et al. |
| 8,137,695 | B2 | 3/2012 | Rozema et al. |
| 8,153,365 | B2 | 4/2012 | Wengel et al. |
| 8,158,601 | B2 | 4/2012 | Chen et al. |
| 8,268,980 | B2 | 9/2012 | Seth et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,313,772 | B2 | 11/2012 | Rozema et al. |
| 8,344,125 | B2 | 1/2013 | Manoharan et al. |
| 8,349,308 | B2 | 1/2013 | Yurkovetskiy et al. |
| 8,404,862 | B2 | 3/2013 | Manoharan et al. |
| 8,435,491 | B2 | 5/2013 | Wang et al. |
| 8,440,803 | B2 | 5/2013 | Swayze et al. |
| 8,450,467 | B2 | 5/2013 | Manoharan et al. |
| 8,501,805 | B2 | 8/2013 | Seth et al. |
| 8,501,930 | B2 | 8/2013 | Rozema et al. |
| 8,530,640 | B2 | 9/2013 | Seth et al. |
| 8,541,548 | B2 | 9/2013 | Rozema |
| 8,546,556 | B2 | 10/2013 | Seth et al. |
| 8,552,163 | B2 | 10/2013 | Lee et al. |
| RE44,779 | E | 2/2014 | Imanishi et al. |
| 8,796,437 | B2 | 8/2014 | Swayze et al. |
| 9,005,906 | B2 | 4/2015 | Swayze et al. |
| 9,012,421 | B2 | 4/2015 | Migawa et al. |
| 2003/0077829 | A1 | 4/2003 | MacLachlan |
| 2003/0119724 | A1 | 6/2003 | Ts'o et al. |
| 2003/0158403 | A1 | 8/2003 | Manoharan et al. |
| 2003/0175906 | A1 | 9/2003 | Manoharan et al. |
| 2004/0024194 | A1 | 2/2004 | Ravikumar |
| 2005/0026192 | A1 | 2/2005 | Moore et al. |
| 2005/0164235 | A1 | 7/2005 | Manoharan et al. |
| 2006/0148740 | A1 | 7/2006 | Platenburg |
| 2006/0183886 | A1 | 8/2006 | Tso et al. |
| 2008/0039618 | A1 | 2/2008 | Allerson et al. |
| 2008/0108801 | A1 | 5/2008 | Manoharan et al. |
| 2008/0206869 | A1 | 8/2008 | Smith et al. |
| 2008/0281041 | A1 | 11/2008 | Rozema et al. |
| 2008/0281044 | A1 | 11/2008 | Manoharan et al. |
| 2009/0203132 | A1 | 8/2009 | Swayze et al. |
| 2009/0203135 | A1 | 8/2009 | Forst et al. |
| 2009/0286973 | A1 | 11/2009 | Manoharan et al. |
| 2010/0240730 | A1 | 9/2010 | Beigelman et al. |
| 2011/0097264 | A1 | 4/2011 | Wang et al. |
| 2011/0097265 | A1 | 4/2011 | Wang et al. |
| 2011/0123520 | A1 | 5/2011 | Manoharan et al. |
| 2011/0207799 | A1 | 8/2011 | Rozema et al. |
| 2011/0269814 | A1 | 11/2011 | Manoharan et al. |
| 2012/0035115 | A1 | 2/2012 | Manoharan et al. |
| 2012/0095075 | A1 | 4/2012 | Manoharan et al. |
| 2012/0101148 | A1 | 4/2012 | Aking et al. |
| 2012/0128760 | A1 | 5/2012 | Manoharan et al. |
| 2012/0136042 | A1 | 5/2012 | Manoharan et al. |
| 2012/0157509 | A1 | 6/2012 | Hadwiger et al. |
| 2012/0165393 | A1 | 6/2012 | Rozema et al. |
| 2012/0230938 | A1 | 9/2012 | Rozema et al. |
| 2013/0004427 | A1 | 1/2013 | El-Sayed et al. |
| 2013/0109817 | A1 | 5/2013 | Yurkovetskiy et al. |
| 2013/0121954 | A1 | 5/2013 | Wakefield et al. |
| 2013/0178512 | A1 | 7/2013 | Manoharan et al. |
| 2013/0203836 | A1 | 8/2013 | Rajeev et al. |
| 2013/0236968 | A1 | 9/2013 | Manoharan et al. |
| 2015/0191727 | A1 | 7/2015 | Migawa et al. |

FOREIGN PATENT DOCUMENTS

| | | | | |
|---|---|---|---|---|
| WO | WO 1998/013381 | | 4/1998 | |
| WO | WO 1999/014226 | | 3/1999 | |
| WO | WO-0047593 | A1 * | 8/2000 | ............. C07H 21/00 |
| WO | 2000055179 | A1 | 9/2000 | |
| WO | WO 2002/043771 | | 6/2002 | |
| WO | WO 2004/024757 | | 3/2004 | |
| WO | WO 2004/101619 | | 11/2004 | |
| WO | WO 2004/106356 | | 12/2004 | |
| WO | WO 2007/134181 | | 11/2007 | |
| WO | WO 2008/098788 | | 8/2008 | |
| WO | WO 2008/101157 | | 8/2008 | |
| WO | WO 2009/082607 | | 7/2009 | |
| WO | WO 2009/126933 | | 10/2009 | |
| WO | WO 2009/134487 | | 11/2009 | |
| WO | WO 2010/054406 | | 5/2010 | |
| WO | WO 2010/088537 | | 8/2010 | |
| WO | WO 2010/129709 | | 11/2010 | |
| WO | WO 2010/144740 | | 12/2010 | |
| WO | WO 2010/148013 | | 12/2010 | |
| WO | WO 2011/038356 | | 3/2011 | |
| WO | WO 2011/100131 | | 8/2011 | |
| WO | WO 2011/120053 | | 9/2011 | |
| WO | WO 2011/163121 | | 12/2011 | |
| WO | WO 2012/037254 | | 3/2012 | |
| WO | WO 2012/068187 | | 5/2012 | |
| WO | WO 2012/083046 | | 6/2012 | |
| WO | WO 2012/083185 | | 6/2012 | |
| WO | WO 2012/089352 | | 7/2012 | |
| WO | WO 2012/089602 | | 7/2012 | |
| WO | WO 2012/177947 | | 12/2012 | |
| WO | WO 2013/033230 | | 3/2013 | |
| WO | WO 2013/075035 | | 5/2013 | |
| WO | WO 2013/165816 | | 11/2013 | |
| WO | WO 2013/166121 | | 11/2013 | |
| WO | 2014012081 | A2 | 1/2014 | |
| WO | WO 2014/179620 | | 11/2014 | |
| WO | WO-2014179620 | A1 * | 11/2014 | ......... A61K 31/7088 |
| WO | WO 2015/106128 | | 7/2015 | |
| WO | WO 2017/015555 | | 1/2017 | |

(56) References Cited

FOREIGN PATENT DOCUMENTS

WO WO 2020/236618 11/2020
WO 2020249571 A1 12/2020

OTHER PUBLICATIONS

Biessen et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852.
Braasch et al., "Novel Antisense and Peptide Nucleic Acid Strategies for Controlling Gene Expression" Biochemistry (2002) 41(14): 4503-4510.
Cedillo et al., "Synthesis of 5'-GalNAc-Conjugated Oligonucleotides: A Comparison of Solid and Solution-Phase Conjugation Strategies" Molecules (2017) 22(8): 1-12.
Connolly et al., "Binding and Endocytosis of Cluster Glycosides by Rabbit Hepatocytes" J Biol Chem (1982) 257: 939-945.
Crooke et al., "Pharmacokinetic Properties of Several Novel Oligonucleotide Analogs in mice" J. Pharmacol. Exp. Ther. (1996) 277(2):923-937.
Crooke, St., et al., "Antisense Drug Technology" Second Edition, CRC Press (2008) Chapters 1-28.
Duff et al., "Intrabody Tissue-Specific Delivery of Antisense Conjugates in Animals: Ligand-Linker-Antisense Oligomer Conjugates" Methods in Enzymology (1999) 313: 297-321.
Englisch et al., "Chemically Modified Oligonucleotides as Probes and Inhibitors" Agnew Chem. Int. Ed. Engl. (1991) 30:613-629.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
International Search Report for PCT/US20/033196 dated Oct. 1, 2020.
Jayaprakash et al., "Non-Nucleoside Building Blocks for Copper-Assisted and Copper-Free Click Chemistry for the Efficient Synthesis of RNA Conjugates" Organic Letters (2010) 12(23): 5410-5413.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.
Kato et al., "N-acetylgalactosamine incorporation into a peptide containing consecutive threonine residues by UDP-N-acetyl-D-galactosaminide:polypeptide N-acetylgalactosaminyltransferases" Glyobiology (2001) 11: 821-829.
Khorev et al., "Trivalent, Gal/GalNAc-containing ligands designed for the asialoglycoprotein receptor" Bioorganic & Medicinal Chemistry (2008) 16: 5216-5231.
Kim et al., "Oligomeric Glycopeptidomimetics Bearing the Cancer Related TN-Antigen" Tetrahedron Letters (1997) 38(20): 3487-3490.
Kornilova et al., "Development of a fluorescence polarization binding assay for asialoglycoprotein receptor" Analytical Biochemistry (2012) 425: 43-46.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Lee et al., "Synthesis of some cluster glycosides suitable for attachment to proteins or solid matrices" Carbohydrate Research (1978) 67: 509-514.
Lee et al., "Facile Synthesis of a High-Affinity Ligand for Mammalian Hepatic Lectin Containing Three Terminal N-Acetylgalactosamine Residues" Bioconjugate Chem. (1997) 8: 762-765.
Lee et al., "New and more efficient multivalent glyco-ligands for asialoglycoprotein receptor of mammalian hepatocytes" Bioorganic & Medicinal Chemistry (2011) 19:2494-2500.
Lee et al., "Preparation of Cluster Glycosides of Nacetylgalactosamine That Have Subnanomolar Binding Constants Towards the Mammalian Hepatic Gal/GalNAc-specific Receptor" Glycoconjugate J. (1987) 4: 317-328.
Lee et al., "Synthesis of Peptide-Based Trivalent Scaffold for Preparation of Cluster Glycosides" Methods in Enzymology (2003) 362: 38-43.
Lee et al., "New synthetic cluster ligands for galactose/N-acetylgalactosamine-specific lectin of mammalian liver" Biochem (1984) 23: 4255-4261.
Lee et al., "Protein microarrays to study carbohydrate-recognition events" Bioorg Med Chem Lett (2006) 16(19): 5132-5135.
Lee et al., "Synthesis of multivalent neoglyconjugates of MUC1 by the conjugation of carbohydrate-centered, triazole-linked glycoclusters to MUC1 peptides using click chemistry." J Org Chem (2012) 77: 7564-7571.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Maier et al., "Synthesis of Antisense Oligonucleotides Conjugated to a Multivalent Carbohydrate Cluster for Cellular Targeting" Bioconjugate Chem. (2003) 14: 18-29.
Maierhofer et al., "Probing multivalent carbohydrate-lectin interactions by an enzyme-linked lectin assay employing covalently immobilized carbohydrates" Bioorganic & Medicinal Chemistry (2007) 15: 7661-7676.
Manoharan et al., "Cholic Acid-Oligonucleotide Conjugates for Antisense Applications" Bioorg. Med. Chem. Lett. (1994) 4:1053-1060.
Manoharan et al., "Chemical Modifications to Improve Uptake and Bioavailability of Antisense Oligonucleotides" Ann. N.Y. Acad. Sci. (1992) 660: 306-309.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Manoharan et al., "Oligonucleotide Conjugates: Alteration of the Pharmacokinetic Properties of Antisense Agents" Nucleosides & Nucleotides (1995) 14(3-5):969-973.
Manoharan, "Oligonucleotide Conjugates as Potential Antisense Drugs with Improved Uptake, Biodistribution, Targeted Delivery, and Mechanism of Action" Antisense & Nucleic Acid Drug Development (2002) 12: 103-128.
Merwin et al., "Targeted delivery of DNA using YEE(GalNAcAH)3, a synthetic glycopeptide ligand for the asialoglycoprotein receptor." Bioconjug Chem (1994) 5(6): 612-620.
Mishra et al., "Improved leishmanicidal effect of phosphorotioate antisense oligonucleotides by LDL-mediated delivery" Biochim. Biophys. Acta (1995) 1264:229-237.
Nishina et al., "Chimeric Antisense Oligonucleotide Conjugated to α-Tocopherol" *Molecular Therapy Nucleic Acids* (2015) 4: e220.
Nishina et al., "Efficient In Vivo Delivery of siRNA to the Liver by Conjugation of α-Tocopherol" Molecular Therapy (2008) 16: 734-740.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Oka et al., "An Oxazaphospholidine Approach for the Stereocontrolled Synthesis of Oligonucleoside and Phosphorothioates" JACS (2003) 125: 8307-8317.

(56) References Cited

OTHER PUBLICATIONS

Pavia et al., "Synthetic TN glycopeptide related to human glycophorin AM. High-field proton and carbon-13 nuclear magnetic resonance study." Int J Pep Protein Res (1983) 22: 539-548.
Pujol et al., "A Sulfur Tripod Glycoconjugate that Releases a High-Affinity Copper Chelator in Hepatocytes" Angew. Chem. Int. Ed. (2012) 51: 7445-7448.
Rajur et al., "Covalent Protein-Oligonucleotide Conjugates for Efficient Delivery of Antisense Molecules" Bioconjugate Chem. (1997) 8: 935-940.
Rensen et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808.
Rensen et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584.
Rensen et al., "Stimulation of Liver-Directed Cholesterol Flux in Mice by Novel N-Acetylgalactosamine-Terminated Glycolipids With High Affinity for the Asialoglycoprotein Receptor" Arterioscler Thromb Vasc Biol (2006) 26: 169-175.
Rodriguez "Improved Oxidizer Formulations for the Synthesis of PO/PS Mixed Backbone Oligonucleotides" Presentation for TIDES (Boston) Sep. 23, 2021.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sakaki et al., "Human Transthyretin (Prealbumin) Gene and Molecular Genetics of Familial Amyloidotic Polyneruopathy" Mol Biol Med. (1989) 6: 161-168.
Sanghvi, Chapter 15, Antisense Research and Applications, Crooke and Lebleu ed., CRC Press (1993) 273-288.
Maddry et al., "Synthesis of Nonionic Oligonucleotide Analogues" Carbohydrate Modifications in Antisense Research, ACS Symposium: (1994) Chapters 3 & 4.
Sato et al., "Glycoinsulins: Dendritic Sialyloligosaccharide-Displaying Insulins Showing a Prolonged Blood-Sugar-Lowering Activity" J. Am. Chem. Soc. (2004) 126: 14013-14022.
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Sliedregt et al., "Design and Synthesis of Novel Amphiphilic Dendritic Galactosides for Selective Targeting of Liposomes to the Hepatic Asialoglycoprotein Receptor" J. Med. Chem. (1999) 42:609-618.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Tomiya et al., "Liver-targeting of primaquine-(poly-c-glutamic acid) and its degradation in rat hepatocytes" Bioorganic & Medicinal Chemistry (2013) 21: 5275-5281.
Toyokuni et al., "Synthetic vaccines: I. Synthesis of multivalent Tn antigen cluster-lysyllysine conjugates" Tetrahedron Lett (1990) 31(19): 2673-2676.
Valentijn et al., "Solid-phase Synthesis of Lysine-based Cluster Galactosides with High Affinity for the Asialoglycoprotein Receptor" Tetrahedron (1997) 53(2): 759-770.
Van Rossenberg et al., "Stable polyplexes based on arginine-containing oligopeptides for in vivo gene delivery" Gene Ther (2004) 11: 457-464.
Vester et al., "Chemically modified oligonucleotides with efficient RNase H response" Bioorg. Med. Chem. Letters (2008) 18: 2296-2300.
Wan et al. "Synthesis, biophysical properties and biological activity of second generation antisense oligonucleotides containing chiral phosphorothioate linkages" Nuc. Acid. Res. (2014) 42: 13456-13468.
Westerlind et al., "Ligands of the asialoglycoprotein receptor for targeted gene delivery, part 1: Synthesis of and binding studies with biotinylated cluster glycosides containing N-acetylgalactosamine" Glycoconjugate Journal (2004) 21: 227-241.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Beaucage et al., "Advances in the Synthesis of Oligonucleotides by the Phosphoramidite Approach" Tetrahedron (1992) 48: 2223-2311.
Extended EP Search Report for 20810107.1 dated Apr. 21, 2023, 8 pages.
Farrance et al., "Improved chemistry for oligodeoxyribonucleotide synthesis substantially improves restriction enzyme cleavage of a synthetic 35mer" Nucleic Acids Res (1989) 17: 1231-1245.
Pon et al., "An improved iodine/water oxidation reagent for automated oligonucleotide synthesis" Nucleic Acids Res (1987) 15: 7203, 1 page.

* cited by examiner

SYNTHESIS OF OLIGOMERIC COMPOUNDS COMPRISING PHOSPHOROTHIOATE DIESTER AND PHOSPHODIESTER LINKAGES

SEQUENCE LISTING

The present application is being filed along with a Sequence Listing in electronic format. The Sequence Listing is provided as a file entitled DVCM0045USASEQ_ST25.TXT created Nov. 8, 2021 which is 4 kb in size. The information in the electronic format of the sequence listing is incorporated herein by reference in its entirety.

FIELD

The present disclosure provides methods for synthesizing oligomeric compounds having at least one phosphorothioate diester linkage and at least one phosphate diester internucleoside linkage.

BACKGROUND

Oligonucleotides are short oligomers that can be chemically synthesized for research or medical purposes. Oligonucleotides are typically prepared by a stepwise addition of nucleotide residues to produce linked nucleosides having a specific sequence.

Current solid-phase synthesis manufacturing processes of phosphorothioate diester linked oligonucleotides typically use repetition of either three or four-reactions per cycle, namely (1) deprotection (e.g., detritylation); (2) coupling, which results in addition of nucleotide through a phosphite triester bond; (3) sulfurization, which converts the phosphite triester bond to a phosphorothioate triester bond; and optionally (4) capping. Once all of the desired nucleosides have been added, the oligonucleotide is treated with an aliphatic amine to convert phosphorothioate triester bonds into phosphorothioate diester bonds, and then the oligonucleotide is cleaved from the solid support.

Current solid-phase synthesis manufacturing processes of phosphate diester oligonucleotides also uses repetition of the same three or four-reaction cycle, except that for phosphate diester linked oligonucleotides, the sulfurization reaction is replaced by an oxidation reaction, in which the phosphite triester is converted to a phosphate triester. Once all of the desired nucleosides have been added, the oligonucleotide is treated with an aliphatic amine to convert phosphate triester bonds into phosphate diester bonds, and then the oligonucleotide is cleaved from the solid support.

To synthesize oligonucleotides having both phosphate diester internucleoside linkages and phosphorothioate diester internucleoside linkages, one uses a sulfurizing reagent or oxidizing reagent at the appropriate step of the cycle. In certain such circumstances, one will add a phosphate triester bond to a growing oligonucleotide that already has at least one phosphorothioate triester bond. This requires exposing the existing phosphorothioate bond to the oxidizing reagent. At this step, the oxidation reagent can convert the existing phosphorothioate linkage to an undesired phosphate linkage, ultimately resulting in an oligonucleotide having a phosphate diester linkage at one position where phosphorothioate diester linkage was desired.

Therefore, new oxidation reagents and synthetic methods for preparing oligonucleotides containing both phosphorothioate diester linkages and phosphate diester linkages are needed.

SUMMARY

The present disclosure provides synthetic methods for preparing oligonucleotides containing both at least one phosphorothioate diester linkage and at least one phosphate diester linkage. In certain embodiments, the present disclosure provides oxidation reagents for the synthesis of oligonucleotides containing both at least one phosphorothioate diester linkage and at least one phosphate diester linkage with limited amounts of unwanted phosphate diester impurities.

Solid phase oligonucleotide synthesis occurs in a three or four step process where the nucleosides are sequentially linked together from the 3'-end of the oligonucleotide to the 5'-end of the oligonucleotide. For solid phase synthesis, the 3'-most terminal nucleoside is attached to a solid support at the 3' position of the sugar, either directly or through a linker. The 5'-hydroxy of the 3'-most terminal nucleoside is then deprotected (step 1), and then coupled with the next nucleoside (step 2). As a result of the coupling reaction, the nucleosides are linked through a 5'-3' phosphite triester bond. The phosphite triester is then exposed to either a sulfurization agent or an oxidation agent (step 3). Exposure to a sulfurization agent converts the phosphite triester into a phosphorothioate triester; whereas exposure to an oxidation agent converts the phosphite triester into a phosphate triester. Any nucleosides that fail to couple are optionally capped (step 4) and prevented from reacting in further reaction cycles to make them easier to remove during purification. This process is then repeated for each remaining nucleoside in the oligonucleotide.

Accordingly, during the oligonucleotide synthesis process, linkages that will ultimately be phosphate diester linkages in the final oligonucleotide are protected as phosphate triesters and linkages that will ultimately be phosphorothioate diester linkages in the final oligonucleotide are protected as phosphorothioate triesters. Once all of the desired nucleosides have been added, the oligonucleotide is treated with an aliphatic amine to convert phosphate triester linkages and phosphorothioate triester bonds into phosphate diester and phosphorothioate diester bonds, respectively and then the oligonucleotide is cleaved from the solid support. Therefore, during the iterative oligonucleotide synthesis process, both phosphate triester linkages and phosphorothioate triester linkages are added to the growing oligonucleotide during the different cycles of synthesis process. In certain embodiments, the present disclosure provides oxidation reagents that react with only a small percentage of any phosphorothioate triester linkages present in the oligonucleotide during synthesis.

An oxidizing agent commonly used to convert the phosphite triester bond to phosphate triester bond during ASO synthesis is a mixture of pyridine, water, and iodine. However, it is shown herein that use of freshly made mixtures of pyridine, water, and iodine can result in high percentage of the oligonucleotides containing unwanted additional phosphate diester linkages. This results from conversion of phosphorothioate linkages to phosphate linkages upon exposure to the oxidizing reagent. To avoid this unwanted impurity, the pyridine, water, and iodine reagent must be aged for at least 50 days before it can be used as an oxidation reagent during oligonucleotide synthesis as shown herein. The present disclosure provides several different oxidation reagents that can be used to produce highly pure oligonucleotides that contain only a low percentage of unwanted phosphate diester linkages. Unlike the pyridine, water, and iodine oxidizing reagents used in the art, the oxidizing reagents described herein can be used promptly upon their preparation, in certain embodiments within a week; in certain embodiments, within a day; in certain embodiments, within a few hours or immediately upon preparation. In certain embodiments, adding an iodide source to a pyridine, water, and iodine oxidizing reagent results in an oxidizing reagent that can be used promptly upon preparation.

The present disclosure provides the following non-limiting embodiments:

Embodiment 1. A process for synthesizing an oligonucleotide comprising contacting a first oligonucleotide intermediate having a phosphite triester linkage with an oxidizing agent to form a second oligonucleotide intermediate having a phosphate triester linkage.

Embodiment 2. A process for synthesizing an oligomeric compound comprising an oligonucleotide and a 5' conjugate, comprising contacting a first oligonucleotide intermediate having a 5'-phosphite triester linkage with an oxidizing agent to form a second oligonucleotide intermediate having a 5'-phosphate triester linkage.

Embodiment 3. The process of embodiment 1 or 2, wherein the first oligonucleotide intermediate and the second oligonucleotide intermediate are attached to a solid support.

Embodiment 4. A process for preparing a second oligonucleotide intermediate comprising:

a) exposing a first oligonucleotide intermediate having Formula (I):

(I)

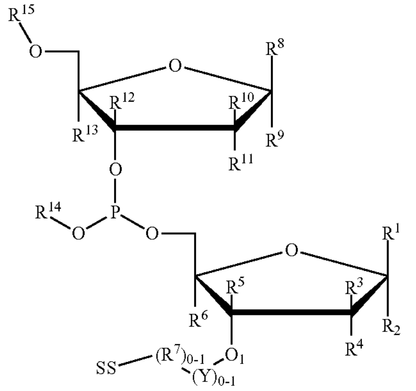

to an oxidizing agent to form a second oligonucleotide intermediate having Formula (II):

(II)

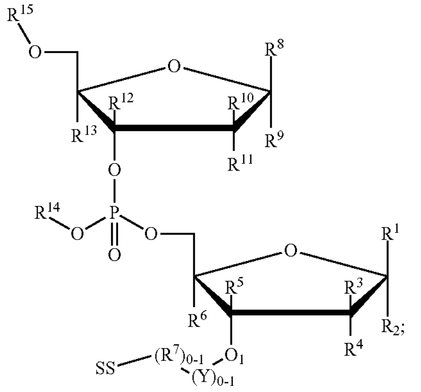

wherein each $R^1$ and $R^8$ is independently a nucleobase or H;

each $R^2$, $R^3$, $R^5$, $R^9$, $R^{10}$, and $R^{12}$, is independently selected from: H, OH, $CH_3$, and F;

$R^{11}$ is selected from: H, $OCH_2CH_2OCH_3$, a halogen, a substituted $C_{1-6}$ alkoxy; a $C_{1-6}$ alkoxy, and a $C_{1-6}$ alkoxy optionally substituted with a $C_{1-6}$ alkoxy; or $R^{11}$ forms a ring with $R^{13}$;

$R^7$ comprises an internucleoside linking group;

SS is a solid support;

$R^6$ is H, OH, $CH_3$, F, or forms a ring with $R^4$;

$R^4$ is selected from: H, a halogen, a substituted $C_{1-6}$ alkoxy $C_{1-6}$ alkoxy, and $C_{1-6}$ alkoxy optionally substituted with $C_{1-6}$ alkoxy or forms a ring with $R^6$ ;

Y is selected from: a nucleotide having a 5'-3'-phosphorothioate diester linkage formed with $O_1$, or an oligonucleotide comprising 2-40 linked nucleosides and having one or more 5'-3' phosphorothioate diester linkages;

$R^{15}$ is a hydroxy protecting group;

$R^{14}$ is $C_{1-6}$ alkyl optionally substituted with —CN;

$R^{13}$ is H, OH, $CH_3$, F, or forms a ring with $R^{11}$;

and thereby preparing a second oligonucleotide intermediate.

Embodiment 5. A process of preparing a second oligonucleotide intermediate comprising:

a) oxidizing a first oligonucleotide intermediating having Formula (III):

(III)

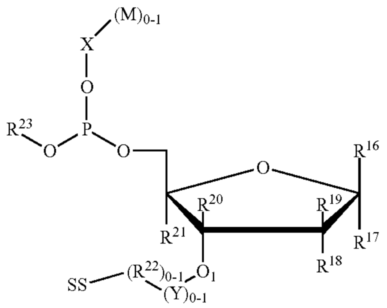

by exposing the compound to an oxidizing agent to form a second oligonucleotide intermediate having Formula (IV):

(IV)

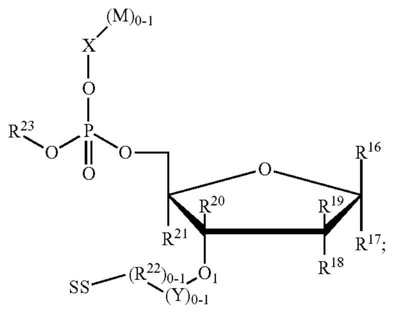

wherein $R^{16}$ is a nucleobase or H;

each $R^{19}$ and $R^{20}$ is independently selected from H, OH, $CH_3$, and F;

$R^{18}$ is selected from: H, a halogen, $C_{1-6}$ alkoxy, a substituted $C_{1-6}$ alkoxy, and $C_{1-6}$ alkoxy optionally substituted with $C_{1-6}$ alkoxy, or forms a ring with $R^{21}$;

$R^{22}$ is an internucleoside linking group;

SS is a solid support;

$R^{21}$ is selected from: H, OH, $CH_3$, and F, or forms a ring with $R^{18}$;

$R^{23}$ is $C_{1-6}$ alkyl optionally substituted with —CN;

Y is selected from a nucleotide having a 5'-3'-phosphorothioate diester linkage formed with $O_1$, or an oligonucleotide comprising 2-40 linked nucleosides having one or more 5'-3' phosphorothioate diester linkages;

X is part of a conjugate linker; and

M is a conjugate moiety;

and thereby preparing the second oligonucleotide intermediate.

Embodiment 6. A process for preparing a second oligonucleotide intermediate comprising:

a) oxidizing a first oligonucleotide intermediate having Formula (I):

(I)

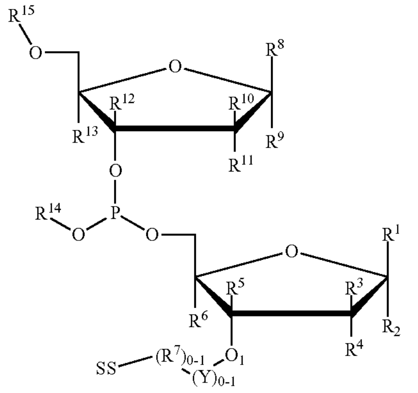

by exposing the compound to an oxidizing agent to form a second oligonucleotide intermediate having Formula (II):

(II)

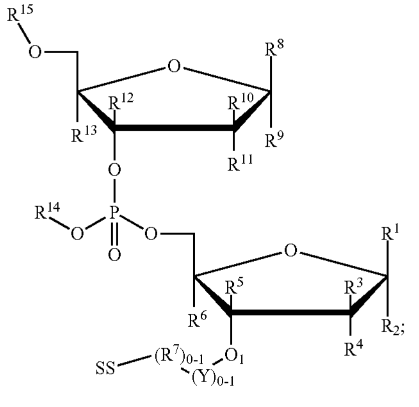

wherein each $R^1$ and $R^8$ is independently a nucleobase or H;

each $R^2$, $R^3$, $R^5$, $R^9$, $R^{10}$, and $R^{12}$, is independently selected from: H, OH, $CH_3$, and F;

$R^{11}$ is selected from: H, a halogen, a substituted $C_{1-6}$ alkoxy $C_{1-6}$ alkoxy, and $C_{1-6}$ alkoxy optionally substituted with $C_{1-6}$ alkoxy, or forms a ring with $R^{13}$;

$R^7$ comprises an internucleoside linking group;

SS is a solid support;

$R^6$ is H, OH, $CH_3$, F, or forms a ring with $R^4$;

$R^4$ is selected from: H, a halogen, a substituted $C_{1-6}$ alkoxy $C_{1-6}$ alkoxy, and $C_{1-6}$ alkoxy optionally substituted with $C_{1-6}$ alkoxy or forms a ring with $R^6$;

Y is selected from: a nucleotide having a 5'-3'-phosphorothioate diester linkage formed with $O_1$, or an oligonucleotide comprising 2-40 linked nucleosides and having one or more 5'-3' phosphorothioate diester linkages;

$R^{15}$ is a hydroxy protecting group;

$R^{14}$ is $C_{1-6}$ alkyl optionally substituted with —CN;

$R^{13}$ is H, OH, $CH_3$, F, or forms a ring with $R^{11}$;

and thereby preparing a second oligonucleotide intermediate.

Embodiment 7. A process of preparing a second oligonucleotide intermediate comprising:

a) oxidizing a first oligonucleotide intermediating having Formula (III):

(III)

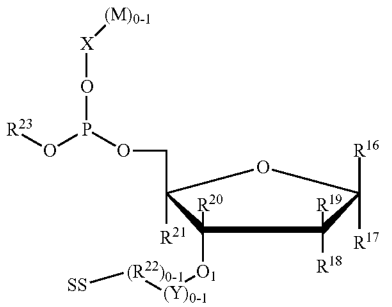

by exposing the compound to an oxidizing agent to form a second oligonucleotide intermediate having Formula (IV):

(IV)

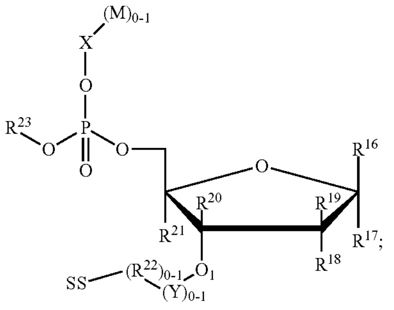

wherein $R^{16}$ is a nucleobase or H;

each $R^{19}$ and $R^{20}$ is independently selected from H, OH, $CH_3$, and F;

$R^{18}$ is selected from: H, a halogen, $C_{1-6}$ alkoxy, a substituted $C_{1-6}$ alkoxy, and $C_{1-6}$ alkoxy optionally substituted with $C_{1-6}$ alkoxy, or forms a ring with $R^{21}$;

$R^{22}$ is an internucleoside linking group;

SS is a solid support;

$R^{21}$ is selected from: H, OH, $CH_3$, and F, or forms a ring with $R^{18}$;

$R^{23}$ is $C_{1-6}$ alkyl optionally substituted with —CN;

Y is selected from a nucleotide having a 5'-3'-phosphorothioate diester linkage formed with $O_1$, or an oligonucleotide comprising 2-40 linked nucleosides having one or more 5'-3' phosphorothioate diester linkages;

X is part of a conjugate linker; and

M is a conjugate moiety;

and thereby preparing the second oligonucleotide intermediate.

Embodiment 8. The process of any of embodiments 1-7, wherein the oxidizing agent comprises a basic solvent.

Embodiment 9. The process of embodiment 8, wherein the conjugate acid of the basic solvent has a pKa of between 5 and 8.

Embodiment 10. The process of any of embodiments 1-9, wherein the oxidizing agent consists of a mixture of $I_2$, a salt, pyridine, and water.

Embodiment 11. The process of embodiment 10, wherein the oxidizing agent consists of a mixture of $I_2$, a salt, and a 9:1 volumetric ratio of pyridine and water.

Embodiment 12. The process of any of embodiments 10-11, wherein the concentration of the salt is the same as the concentration of the $I_2$.

Embodiment 13. The process of any of embodiments 10-11, wherein the concentration of the salt is less than 90%, 80%, 70%, 60%, 50%, 40%, 30%, 20%, 10%, or 5% of concentration of the $I_2$.

Embodiment 14. The process of any of embodiments 10-13, wherein the $I_2$ concentration is 0.01-0.07 M.

Embodiment 15. The process of any of embodiments 10-13, wherein the $I_2$ concentration is 0.01-0.02 M.

Embodiment 16. The process of any of embodiments 10-13, wherein the $I_2$ concentration is 0.04-0.06 M.

Embodiment 17. The process of embodiment 16, wherein the $I_2$ concentration is 0.05M.

Embodiment 18. The process of any of embodiments 10-17, wherein the concentration of the salt is 0.001-0.07 M.

Embodiment 19. The process of embodiment 18, wherein the concentration of the salt is 0.001-0.07 M, 0.005-0.07 M, 0.01-0.07 M, 0.01-0.02M, 0.01-0.06 M, 0.02-0.06 M, 0.03-0.06 M, or 0.04-0.06 M.

Embodiment 20. The process of embodiment 19, wherein the concentration of the salt is 0.04-0.06 M.

Embodiment 21. The process of embodiment 19, wherein the concentration of the salt is 0.05 M.

Embodiment 22. The process of any of embodiments 10-21, wherein the salt is a halide salt.

Embodiment 23. The process of embodiment 22, wherein the halide is bromide, chloride, or fluoride.

Embodiment 24. The process of embodiment 22, wherein the halide is iodide.

Embodiment 25. The process of embodiment 24, wherein the salt is NaI, KI, LiI, or pyridinium iodide.

Embodiment 26. The process of embodiment 25, wherein the salt is NaI.

Embodiment 27. The process of embodiment 25, wherein the salt is KI.

Embodiment 28. The process of embodiment 25, wherein the salt is LiI.

Embodiment 29. The process of embodiments 24-26, wherein the oxidizing agent consists of 0.05 M $I_2$ and 0.05 M NaI dissolved in a 9:1 volumetric ratio of pyridine and water.

Embodiment 30. The process of embodiments 24-25 or 27, wherein the oxidizing agent consists of 0.05 M $I_2$ and 0.05 M KI dissolved in a 9:1 volumetric ratio of pyridine and water.

Embodiment 31. The process of embodiments 24-25 or 28, wherein the oxidizing agent consists of 0.05 M $I_2$ and 0.05 M KI dissolved in a 9:1 volumetric ratio of pyridine and water.

Embodiment 32. The process of any of embodiments 1-31, wherein the oxidizing agent was prepared less than 60 days before oxidizing the compound of Formula (I) or the compound of Formula (III).

Embodiment 33. The process of any of embodiments 1-31, wherein the oxidizing agent is prepared less than 50 days before oxidizing the compound of Formula (I) or the compound of Formula (III).

Embodiment 34. The process of any of embodiments 1-31, wherein the oxidizing agent is prepared less than 30 days before oxidizing the compound of Formula (I) or the compound of Formula (III).

Embodiment 35. The process of any of embodiments 1-31, wherein the oxidizing agent is prepared less than 28 days before oxidizing the compound of Formula (I) or the compound of Formula (III).

Embodiment 36. The process of any of embodiments 1-31, wherein the oxidizing agent is prepared less than 14 days before oxidizing the compound of Formula (I) or the compound of Formula (III).

Embodiment 37. The process of any of embodiments 1-31, wherein the oxidizing agent is prepared less than 7 days before oxidizing the compound of Formula (I) or the compound of Formula (III).

Embodiment 38. The process of any of embodiments 1-31, wherein the oxidizing agent is prepared less than 48 hours before oxidizing the compound of Formula (I) or the compound of Formula (III).

Embodiment 39. The process of any of embodiments 1-31, wherein the oxidizing agent is prepared less than 24 hours before oxidizing the compound of Formula (I) or the compound of Formula (III).

Embodiment 40. The process of any of embodiments 1-39, wherein the compound of Formula I or Formula III is exposed to the oxidation agent for between 1 and 15 minutes.

Embodiment 41. The process of any of embodiments 1-40, wherein the compound of Formula I or Formula III is exposed to the oxidation agent for between 3 and 5 minutes.

Embodiment 42. The process of any of embodiments 1-40, wherein the compound of Formula I or Formula III is exposed to the oxidation agent for at least 10 minutes.

Embodiment 43. The process of any of embodiments 4, 6, or 8-42, wherein $R^1$ is selected from: thymine, uracil, guanine, cytosine, 5-methylcytosine, and adenine.

Embodiment 44. The process of any of embodiments 4, 6 or 8-42, wherein $R^4$ is selected from: —H, —OH, —$OCH_3$, —F, —$OCH_2C(=O)$—$NH(CH_3)$, and —$O(CH_2)_2CH_3$.

Embodiment 45. The process of any of embodiments 4, 6 or 8-42, wherein each of $R^2$, $R^3$, $R^5$, and $R^6$ is H.

Embodiment 46. The process of any of embodiments 4, 6 or 8-43, wherein $R^6$ forms a ring with $R^4$ and wherein the bridging group between $R^6$ and $R^4$ is 4'-$CH_2$—O-2'.

Embodiment 47. The process of embodiment 46, wherein bicyclic ring is in the β-D configuration.

Embodiment 48. The process of any of embodiments 4, 6 or 8-43, wherein $R^6$ forms a ring with $R^4$ and wherein the bridging group between $R^6$ and $R^4$ is 4'-$CH(CH_3)$—O-2'.

Embodiment 49. The process of embodiment 48, wherein the bicyclic ring is in the β-D configuration and the substituents attached to the bridging carbon are in the (S) configuration.

Embodiment 50. The process of any of embodiments 4, 6 or 8-49, wherein $R^8$ is selected from: thymine, uracil, guanine, cytosine, 5-methylcytosine, and adenine.

Embodiment 51. The process of any of embodiments 4, 6 or 8-50, wherein $R^{11}$ is selected from: —H, —OH, —$OCH_3$, —F, —$OCH_2C(=O)—NH(CH_3)$, and —$O(CH_2)_2OCH_3$.

Embodiment 52. The process of any of embodiments 4, 6 or 8-50, wherein $R^{13}$ forms a ring with $R^{11}$ and wherein the bridging group between $R^{13}$ and $R^{11}$ is 4'-$CH_2$—O—2'.

Embodiment 53. The process of embodiment 52, wherein bicyclic ring is in the β-D configuration.

Embodiment 54. The process of any of embodiments 4, 6 or 8-53, wherein $R^{13}$ forms a ring with $R^{11}$ and wherein the bridging group between $R^6$ and $R^4$ is 4'-$CH(CH_3)$—O-2'.

Embodiment 55. The process of embodiment 54, wherein the bicyclic ring is in the β-D configuration and the substituents attached to the bridging carbon are in the (S) configuration.

Embodiment 56. The process of any of embodiments 4, 6 or 8-55, wherein each of $R^9$, $R^{10}$, $R^{12}$, and $R^{13}$ is H.

Embodiment 57. The process of any of embodiments 4, 6 or 8-55 wherein $R^{14}$ is —$CH_2CH_2C{\equiv}N$.

Embodiment 58. The process of any of embodiments 4, 6 or 8-57, wherein $R^7$ comprises Unylinker™.

Embodiment 59. The process of any of embodiments 4, 6 or 8-58, wherein $R^{15}$ is DMTr.

Embodiment 60. The process of any of embodiments 5, 7 or 8-42, wherein $R^{16}$ is selected from: thymine, uracil, guanine, cytosine, 5-methylcytosine, and adenine.

Embodiment 61. The process of any of embodiments 5, 7-42, or 60, wherein $R^{18}$ is selected from: —H, —OH, —$OCH_3$, —F, —$OCH_2C(=O)—NH(CH_3)$, and —$O(CH_2)_2OCH_3$.

Embodiment 62. The process of any of embodiments 5, 7-42, or 60-61, wherein each of $R^{17}$, $R^{19}$, $R^{20}$, and $R^{21}$ is H.

Embodiment 63. The process of any of embodiments 5, 7-42, or 60-62, wherein $R^{21}$ forms a ring with $R^{18}$ and wherein the bridging group between $R^{21}$ and $R^{18}$ is 4'-$CH_2$—O-2'.

Embodiment 64. The process of any of embodiments 5, 7-42, or 60-63, wherein $R^{21}$ forms a ring with $R^{18}$ and wherein the bridging group between $R^{21}$ and $R^{18}$ is 4'-$CH(CH_3)$—O-2'.

Embodiment 65. The process of any of embodiments 5, 7-42, or 60-64, wherein $R^{23}$ is —$CH_2CH_2C{\equiv}N$.

Embodiment 66. The process of any of embodiments 5, 7-42, or 60-65, wherein X is —C(=O)—$(CH_2)_3$—C(=O)N(H)—$(CH_2)_6$—O—.

Embodiment 67. The process of any of embodiments 5, 7-42, or 60-66, wherein M comprises one or more N-acetyl galactosamine moieties.

Embodiment 68. The process of any of embodiments 5, 7-42, or 60-67, wherein M comprises a group having the structure of Formula (V):

(V)

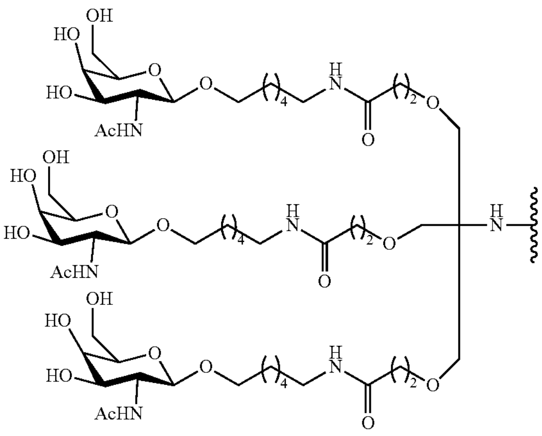

.

Embodiment 69. The process of any of embodiments 4-68, wherein Y is absent.

Embodiment 70. The process of any of embodiments 4-68, wherein Y is an oligonucleotide consisting of at least 5-40 linked nucleosides.

Embodiment 71. The process of any of embodiments 4-68, wherein Y is an oligonucleotide consisting of at least 7 linked nucleosides.

Embodiment 72. The process of any of embodiments 4-68, wherein Y is an oligonucleotide consisting of at least 9 linked nucleosides.

Embodiment 73. The process of any of embodiments 4-68, wherein Y is an oligonucleotide consisting of at least 11 linked nucleosides.

Embodiment 74. The process of any of embodiments 4-68, wherein Y is an oligonucleotide consisting of at least 13 linked nucleosides.

Embodiment 75. The process of any of embodiments 4-68, wherein Y is an oligonucleotide consisting of at least 15 linked nucleosides.

Embodiment 76. The process of any of embodiments 4-68, wherein Y is an oligonucleotide consisting of at least 17 linked nucleosides.

Embodiment 77. The process of any of embodiments 70-76, wherein at least 4 internucleoside linkages of the oligonucleotide are phosphorothioate diester internucleoside linkages.

Embodiment 78. The process of any of embodiments 71-76, wherein at least 5 internucleoside linkages of the oligonucleotide are phosphorothioate diester internucleoside linkages.

Embodiment 79. The process of any of embodiments 72-76, wherein at least 6 internucleoside linkages of the oligonucleotide are phosphorothioate diester internucleoside linkages.

Embodiment 80. The process of any of embodiments 72-76, wherein at least 7 internucleoside linkages of the oligonucleotide are phosphorothioate diester internucleoside linkages.

Embodiment 81. The process of any of embodiments 72-76, wherein at least 8 internucleoside linkages of the oligonucleotide are phosphorothioate diester internucleoside linkages.

Embodiment 82. The process of any of embodiments 72-81, wherein each internucleoside linkage of the oligonucleotide is either a phosphorothioate diester internucleoside linkage or a phosphate diester internucleoside linkage.

Embodiment 83. The process of any of embodiments 1-3, wherein the oligonucleotide consists of at least 5-40 linked nucleosides.

Embodiment 84. The process of any of embodiments 1-3, wherein the oligonucleotide consists of at least 7 linked nucleosides.

Embodiment 85. The process of any of embodiments 1-3, wherein the oligonucleotide consists of at least 9 linked nucleosides.

Embodiment 86. The process of any of embodiments 1-3, wherein the oligonucleotide consists of at least 11 linked nucleosides.

Embodiment 87. The process of any of embodiments 1-3, wherein the oligonucleotide consists of at least 13 linked nucleosides.

Embodiment 88. The process of any of embodiments 1-3, wherein the oligonucleotide consists of at least 15 linked nucleosides.

Embodiment 89. The process of any of embodiments 1-3, wherein the oligonucleotide consists of at least 17 linked nucleosides.

Embodiment 90. The process of any of embodiments 83-89, wherein at least 4 internucleoside linkages of the oligonucleotide are phosphorothioate diester internucleoside linkages.

Embodiment 91. The process of any of embodiments 84-89, wherein at least 5 internucleoside linkages of the oligonucleotide are phosphorothioate diester internucleoside linkages.

Embodiment 92. The process of any of embodiments 84-89, wherein at least 6 internucleoside linkages of the oligonucleotide are phosphorothioate diester internucleoside linkages.

Embodiment 93. The process of any of embodiments 85-89, wherein at least 7 internucleoside linkages of the oligonucleotide are phosphorothioate diester internucleoside linkages.

Embodiment 94. The process of any of embodiments 85-89, wherein at least 8 internucleoside linkages of the oligonucleotide are phosphorothioate diester internucleoside linkages.

Embodiment 95. The process of any of embodiments 83-94, wherein each internucleoside linkage of the oligonucleotide is either a phosphorothioate diester internucleoside linkage or a phosphate diester internucleoside linkage.

Embodiment 96. The process of any of embodiments 4-84, wherein the oligonucleotide intermediate undergoes one or more further reactions.

Embodiment 97. The process of embodiment 96, wherein the one or more further reactions comprises a capping reaction.

Embodiment 98. The process of embodiment 97, wherein the capping reaction comprises exposing the oligonucleotide intermediate to acetic anhydride.

Embodiment 99. The process of any of embodiment 96-108, wherein the capping reaction comprises exposing the oligonucleotide intermediate to a basic catalyst.

Embodiment 100. The process of embodiment 99, wherein the basic catalyst is pyridine.

Embodiment 101. The process of any of embodiments 96-100, wherein the one or more further reactions comprises a detritylation reaction.

Embodiment 102. The process of embodiment 101, wherein the detritylation reaction comprises exposing the oligonucleotide intermediate to dichloroacetic acid.

Embodiment 103. The process of any of embodiments 96-102, wherein the one or more further reactions comprises coupling the oligonucleotide intermediate to a phosphoramidite.

Embodiment 104. The process of any of embodiments 96-102, wherein the one or more further reactions comprises cleaving the oligonucleotide intermediate from the solid support.

Embodiment 105. The process of any of embodiments 96-104, wherein the one or more further reactions comprises deprotecting any triester linkages on the oligonucleotide intermediate.

Embodiment 106. The process of embodiment 105, wherein the oligonucleotide intermediate undergoes multiple further reactions to yield a modified oligonucleotide.

Embodiment 107. The process of embodiment 106, wherein the modified oligonucleotide is a gapmer.

Embodiment 108. The process of any of embodiments 1-5 or 8-68 or 83-95, wherein the second oligonucleotide intermediate undergoes one or more further reactions.

Embodiment 109. The process of embodiment 108, wherein the one or more further reactions comprises a capping reaction.

Embodiment 110. The process of embodiment 109, wherein the capping reaction comprises exposing the second oligonucleotide intermediate to acetic anhydride.

Embodiment 111. The process of any of embodiment 109-110, wherein the capping reaction comprises exposing the second oligonucleotide intermediate to a basic catalyst.

Embodiment 112. The process of embodiment 111, wherein the basic catalyst is pyridine.

Embodiment 113. The process of any of embodiments 109-112, wherein the one or more further reactions comprises a detritylation reaction.

Embodiment 114. The process of embodiment 113, wherein the detritylation reaction comprises exposing the second oligonucleotide intermediate to dichloroacetic acid.

Embodiment 115. The process of any of embodiments 109-114, wherein the one or more further reactions comprises coupling the second oligonucleotide intermediate to a phosphoramidite to form a third oligonucleotide intermediate.

Embodiment 116. The process of any of embodiments 109-115, wherein the one or more further reactions comprises cleaving the second oligonucleotide intermediate or a product thereof from the solid support.

Embodiment 117. The process of any of embodiments 108-116, wherein the one or more further reactions comprises deprotecting any triester linkages on the second oligonucleotide intermediate or product thereof.

Embodiment 118. The process of embodiment 117, wherein the second oligonucleotide intermediate undergoes multiple further reactions to yield a modified oligonucleotide.

Embodiment 119. The process of embodiment 118, wherein the modified oligonucleotide is a gapmer.

Embodiment 120. The process of any of embodiments 1-119, wherein the process results in an oligonucleotide product having less than 5% of the $(P{=}O)_1$ impurity.

Embodiment 121. The process of any of embodiments 1-119, wherein the process results in an oligonucleotide product having less than 4% of the $(P{=}O)_1$ impurity.

Embodiment 122. The process of any of embodiments 1-119, wherein the process results in an oligonucleotide product having less than 3% of the $(P{=}O)_1$ impurity.

Embodiment 123. The process of any of embodiments 1-119, wherein the process results in an oligonucleotide product having less than 2% of the $(P{=}O)_1$ impurity.

Embodiment 124. The process of any of embodiments 1-123, wherein the process results in an oligonucleotide product having less than 1%, less than 2%, or less than 5% of the DMTr-C-phosphonate impurity.

DETAILED DESCRIPTION

Figure 1:
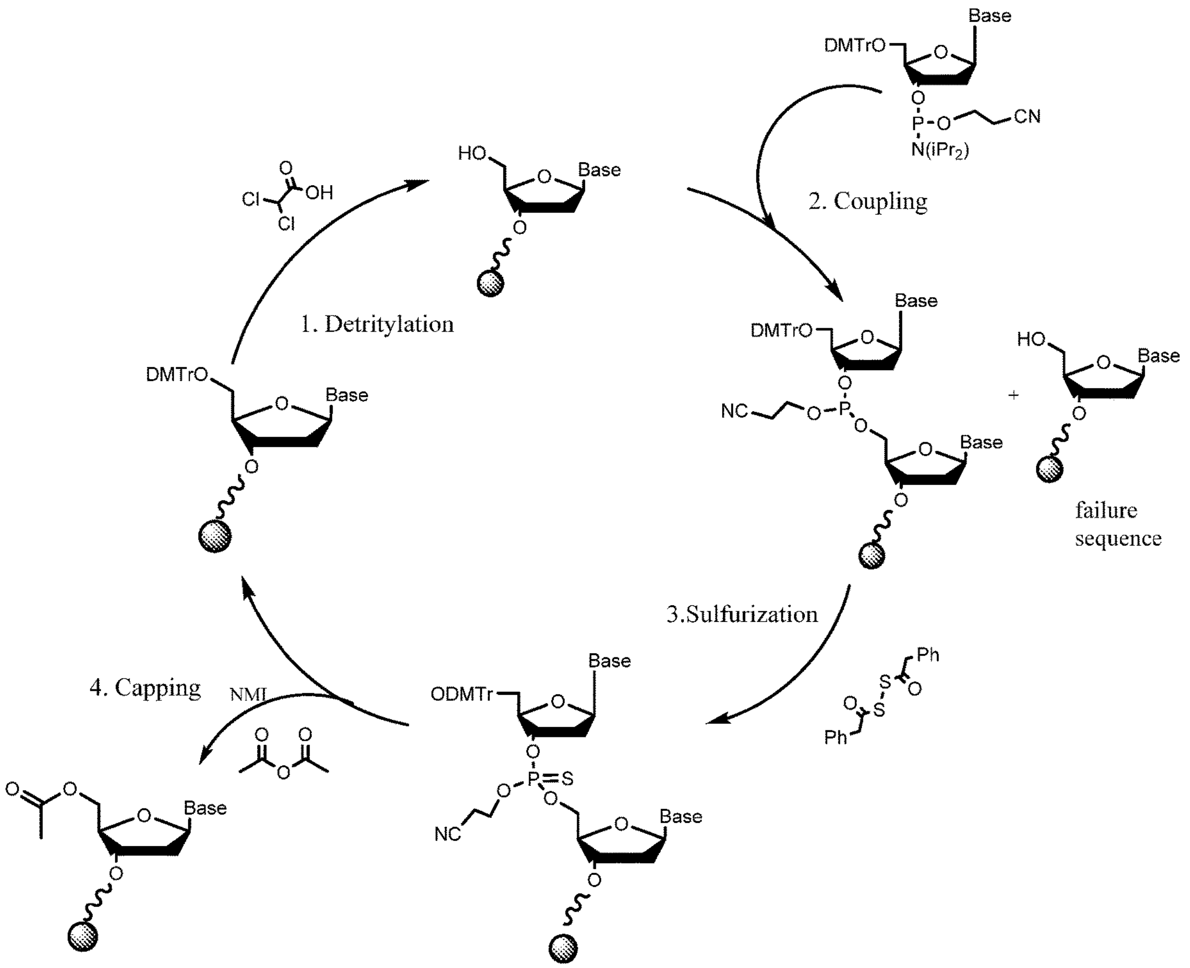
FIG. 1 illustrates the four-reaction cycle for the stepwise addition of adding nucleotide residues. Step 3 in the figure illustrates where the sulfurization reaction occurs to produce a phosphorothioate triester.
Figure 2:
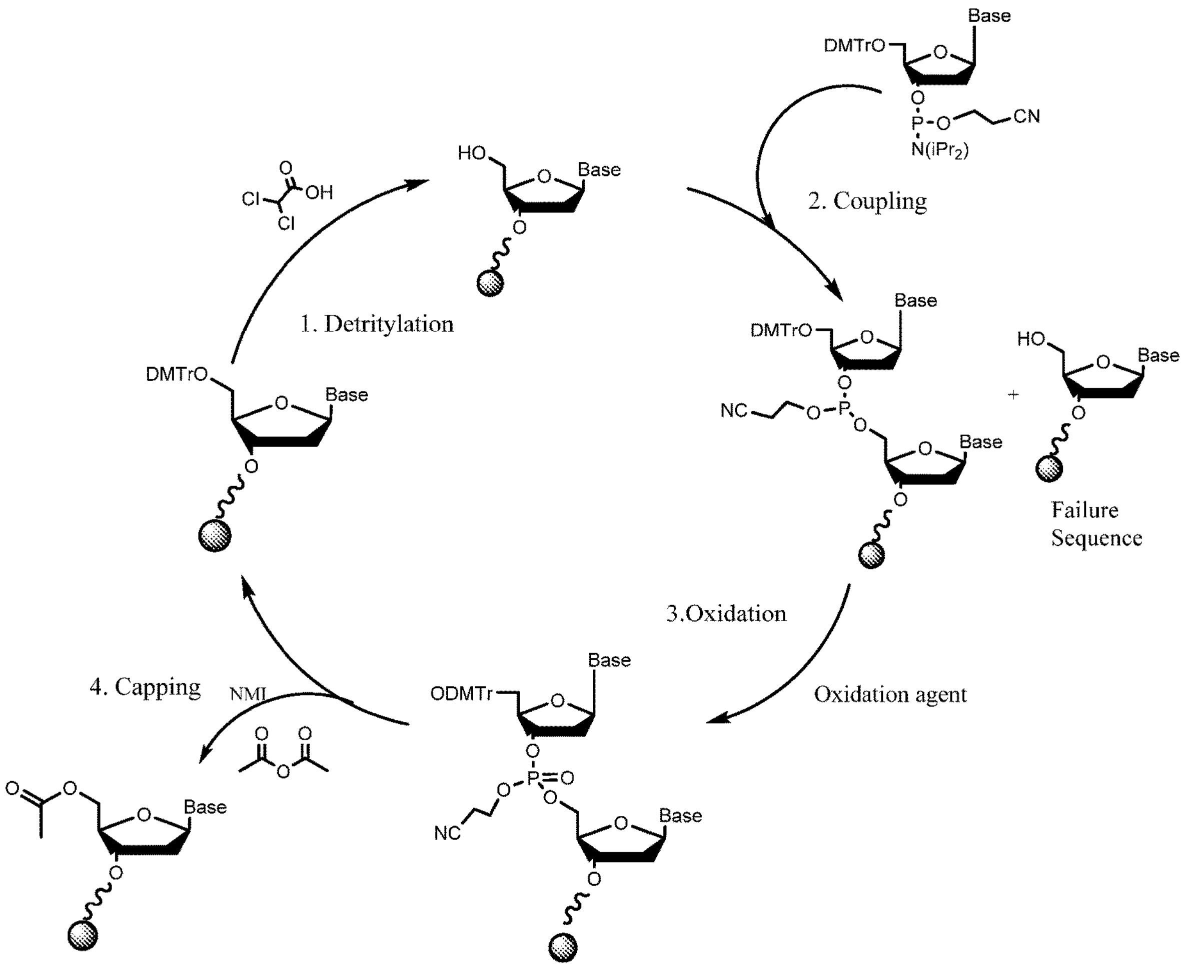
FIG. 2 illustrates the four-reaction cycle for the stepwise addition of adding nucleotide residues. Step 3 in the figure illustrates where the oxidation reaction occurs to produce a phosphate triester.

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase.

As used herein, "2'-deoxyfuranosyl sugar moiety" or "2'-deoxyfuranosyl sugar" means a furanosyl sugar moiety having two hydrogens at the 2'-position. 2'-deoxyfuranosyl sugar moieties may be unmodified or modified and may be substituted at positions other than the 2'-position or unsubstituted. A β-D-2'-deoxyribosyl sugar moiety or 2'-β-D-deoxyribosyl sugar moiety in the context of an oligonucleotide is an unsubstituted, unmodified 2'-deoxyfuranosyl and is found in naturally occurring deoxyribonucleic acids (DNA).

As used herein, "2'-modified" in reference to a furanosyl sugar moiety or nucleoside comprising a furanosyl sugar moiety means the furanosyl sugar moiety comprises a substituent other than H or OH at the 2'-position of the furanosyl sugar moiety. 2'-modified furanosyl sugar moieties include non-bicyclic and bicyclic sugar moieties and may comprise, but are not required to comprise, additional substituents at other positions of the furanosyl sugar moiety.

As used herein, "2'-substituted" in reference to a furanosyl sugar moiety or nucleoside comprising a furanosyl sugar moiety means the furanosyl sugar moiety or nucleoside comprising the furanosyl sugar moiety comprises a substituent other than H or OH at the 2'-position and is a non-bicyclic furanosyl sugar moiety. 2'-substituted furanosyl sugar moieties do not comprise additional substituents at other positions of the furanosyl sugar moiety other than a nucleobase and/or internucleoside linkage(s) when in the context of an oligonucleotide.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety, and the bicyclic sugar moiety is a modified furanosyl sugar moiety. In certain embodiments, the bicyclic sugar moiety does not comprise a furanosyl moiety.

As used herein, "cEt" or "constrained ethyl" means a bicyclic sugar moiety, wherein the first ring of the bicyclic sugar moiety is a ribosyl sugar moiety, the second ring of the bicyclic sugar is formed via a bridge connecting the 4'-carbon and the 2'-carbon, the bridge has the formula 4'-CH$(CH_3)$—O-2', and the bridge is in the S configuration. A cEt bicyclic sugar moiety is in the β-D configuration.

As used herein, "conjugate group" means a group of atoms that is directly or indirectly attached to an oligonucleotide. Conjugate groups may comprise a conjugate moiety and a conjugate linker that attaches the conjugate moiety to the oligonucleotide.

As used herein, "conjugate linker" means a group of atoms comprising at least one bond that connects a conjugate moiety to an oligonucleotide.

As used herein, "conjugate moiety" means a group of atoms that is attached to an oligonucleotide via a conjugate linker.

As used herein, "DMTr-C-phosphonate impurity" means a 4,4'-dimethoxytrityl-C-phosphonate moiety located internally on the oligonucleotide or at the 5'-terminal hydroxy group. During oligonucleotide synthesis, phosphite triester intermediates that fail to oxidize or sulfurize to the corresponding triester then react during the next detritylation step to form the DMTr-C-phosphonate impurity.

As used herein, "double-stranded antisense compound" means an antisense compound comprising two oligomeric compounds that are complementary to each other and form a duplex, and wherein one of the two said oligomeric compounds comprises an antisense oligonucleotide.

As used herein, "gapmer" means an oligonucleotide or a portion of an oligonucleotide having a central region comprising a plurality of nucleosides that support RNase H cleavage positioned between a 5'-region and a 3'-region. Herein, the 3'- and 5'-most nucleosides of the central region each comprise a 2'-deoxyfuranosyl sugar moiety. Herein, the 3'-most nucleoside of the 5'-region comprises a 2'-modified sugar moiety or a sugar surrogate. Herein, the 5'-most nucleoside of the 3'-region comprises a 2'-modified sugar moiety or a sugar surrogate. The "central region" may be referred to as a "gap"; and the "5'-region" and "3'-region" may be referred to as "wings".

As used herein, the terms "internucleoside linkage" means a group or bond that forms a covalent linkage between adjacent nucleosides in an oligonucleotide. As used herein "modified internucleoside linkage" means any internucleoside linkage other than a naturally occurring, phosphate diester internucleoside linkage. Modified internucleoside linkages may or may not contain a phosphorus atom. A "neutral internucleoside linkage" is a modified internucleoside linkage that is mostly or completely uncharged at pH 7.4 and/or has a pKa below 7.4.

As used herein, "abasic nucleoside" means a sugar moiety in an oligonucleotide or oligomeric compound that is not directly connected to a nucleobase. In certain embodiments, an abasic nucleoside is adjacent to one or two nucleosides in an oligonucleotide.

As used herein, "LICA-1" is a conjugate group that is represented by the formula:

nucleobase that can pair with any one of the five unmodified nucleobases. 5-methylcytosine ($^{m}C$) is one example of a modified nucleobase.

As used herein, "nucleobase sequence" means the order of contiguous nucleobases in a nucleic acid or oligonucleotide independent of any sugar moiety or internucleoside linkage modification.

As used herein, "nucleoside" means a moiety comprising a nucleobase and a sugar moiety. The nucleobase and sugar moiety are each, independently, unmodified or modified. As used herein, "modified nucleoside" means a nucleoside comprising a modified nucleobase and/or a modified sugar moiety.

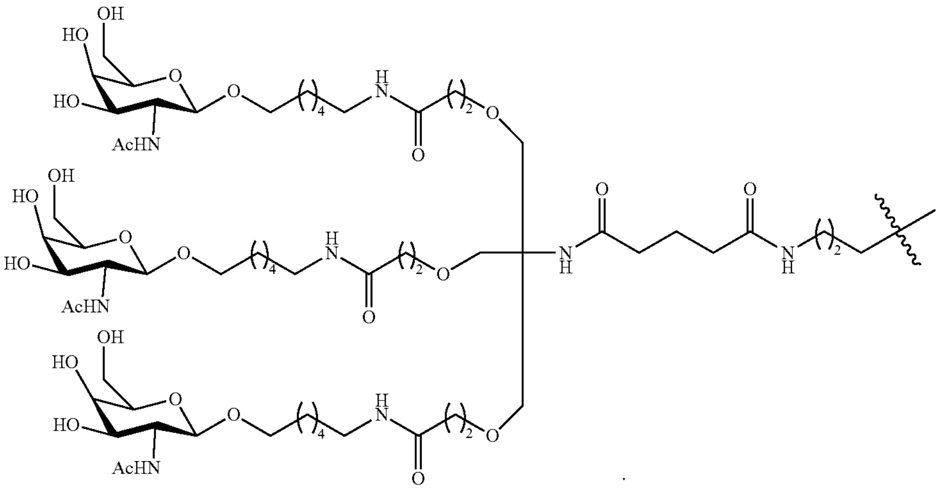

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic sugar" or "non-bicyclic sugar moiety" means a sugar moiety that comprises fewer than 2 rings. Substituents of modified, non-bicyclic sugar moieties do not form a bridge between two atoms of the sugar moiety to form a second ring.

As used herein, "linked nucleosides" are nucleosides that are connected in a continuous sequence (i.e. no additional nucleosides are present between those that are linked).

As used herein, "MOE" means methoxyethyl. "2'-MOE" or "2'-O-methoxyethyl" means a 2'-$OCH_2CH_2OCH_3$ group at the 2'-position of a furanosyl ring. In certain embodiments, the 2'-$OCH_2CH_2OCH_3$ group is in place of the 2'-OH group of a ribosyl ring or in place of a 2'-H in a 2'-deoxyribosyl ring.

As used herein, "naturally occurring" means found in nature.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a modified nucleobase is a group of atoms capable of pairing with at least one unmodified nucleobase. A universal base is a As used herein, "oligomeric compound" means a compound consisting of an oligonucleotide and optionally one or more additional features, such as a conjugate group or terminal group.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 2-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "oligonucleotide product" means a composition comprising a number of constituent oligonucleotides produced after synthesis.

As used herein, "oxidation agent" means any substance which exposed to another molecule removes electrons from the molecule. In certain embodiments, an oxidation agent is any substance which can convert a phosphite triester linkage to a phosphate triester linkage.

As used herein, "phosphate triester linkage" means a linkage in which one of the non-bridging oxygen atoms of a phosphate diester is covalently bound to an alkyl or substituted alkyl.

As used herein, "phosphorothioate diester linkage" means a modified internucleoside linkage in which one of the non-bridging oxygen atoms of a phosphate diester internucleoside linkage is replaced with a sulfur atom.

As used herein, "phosphorothioate triester linkage" means a modified internucleoside linkage in which one of the non-bridging oxygen atoms of a phosphate diester internucleoside linkage is replaced with a sulfur atom and the remaining non-bridging oxygen atom is covalently bound to an alkyl or substituted alkyl.

As used herein, "(P═O) impurity" means an oligonucleotide or portion thereof in which at least one linkage that was intended to be a phosphorothioate diester linkage is instead a phosphate diester linkage.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense oligonucleotides that act through RNase H.

As used herein, the term "single-stranded" in reference to an antisense compound means such a compound consisting of one oligomeric compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex, in which case the compound would no longer be single-stranded.

As used herein, "sugar moiety" means an unmodified sugar moiety or a modified sugar moiety. As used herein, "unmodified sugar moiety" means a β-D-ribosyl moiety, as found in naturally occurring RNA, or a β-D-2'-deoxyribosyl sugar moiety as found in naturally occurring DNA. As used herein, "modified sugar moiety" or "modified sugar" means a sugar surrogate or a furanosyl sugar moiety other than a β-D-ribosyl or a β-D-2'-deoxyribosyl. Modified furanosyl sugar moieties may be modified or substituted at a certain position(s) of the sugar moiety, or unsubstituted, and they may or may not have a stereoconfiguration other than β-D-ribosyl. Modified furanosyl sugar moieties include bicyclic sugars and non-bicyclic sugars. As used herein, "sugar surrogate" means a modified sugar moiety that does not comprise a furanosyl or tetrahydrofuranyl ring (is not a "furanosyl sugar moiety") and that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

Certain Process for the Synthesis of Oligonucleotides

The present disclosure provides synthetic methods for preparing oligonucleotides containing both at least one phosphorothioate diester linkage and at least one phosphate diester linkage. The present disclosure also provides synthetic methods for preparing oligonucleotides having a conjugate moiety attached to the oligonucleotide through a cleavable linker. In certain embodiments, the cleavable linker is a phosphate diester bond. In certain embodiments, oligonucleotides having both at least one phosphorothioate diester linkage and at least one phosphate diester linkage have one or more desired properties. In certain embodiments, oligonucleotides having both at least one phosphorothioate diester linkage and at least one phosphate diester linkage are gapmers. In certain embodiments, oligonucleotides having both at least one phosphorothioate diester linkage and at least one phosphate diester linkage are used to modulate splicing of a nucleic acid target. In certain embodiments, oligonucleotides having both at least one phosphorothioate diester linkage and at least one phosphate diester linkage are RNAi compounds. Such oligonucleotides may comprise any of the features, modified nucleosides, and nucleoside motifs described herein.

Accordingly, such oligonucleotides may comprise any of the modified sugar moieties described herein and/or any of the modified nucleobases. In certain embodiments, the synthetic processes described herein are used to synthesize oligomeric compounds comprising a conjugate group. In certain embodiments, the synthetic processes described herein are used to synthesize oligomeric compounds comprising a conjugate group comprising one or more N-Acetylgalactosamine residues. In certain embodiments, the synthetic processes described herein are used to synthesize oligomeric compounds comprising a conjugate group comprising LICA-1. In certain embodiments, the synthetic processes described herein are used to synthesize oligomeric compounds comprising a conjugate group comprising LICA-1 linked to an oligonucleotide through one or more phosphate diester bonds. In certain embodiments, the oligomeric compounds synthesized using the processes described herein are gapmers. In certain embodiments, they are RNAi compounds. In certain embodiments, they are single-stranded. In certain embodiments, they are double-stranded. In certain embodiments, compounds synthesized using the processes described herein are formulated for administration to an animal.

In certain embodiments, the process is useful for oxidizing a bond within a conjugate group attached to an oligonucleotide. For example, in certain embodiments, the process described herein can oxidize a conjugate linker that comprises a phosphate triester into a conjugate linker that comprises a phosphate diester. Such conjugate groups include, but are not limited to, any of those described herein.

In certain embodiments, the phosphorothioate triester bonds are made using PADS and the phosphate triester bonds are made using an oxidation agent described herein.

The present disclosure provides oxidation reagents that can be used a short time or immediately after preparation to produce highly pure oligonucleotides that contain only a low percentage of the $(P{=}O)_1$ impurity. The present disclosure also provides oxidation reagents that can be used a short time or immediately after preparation to produce highly pure oligonucleotides that contain only a low percentage of the DMTr-C-phosphonate impurity.

Certain Oxidation Reagents for the Synthesis of Oligonucleotides

The present disclosure provides oxidation agents for use in the synthesis of oligonucleotides that produce low amounts of the $(P{=}O)_1$ impurity and which can be used immediately after preparation or within a day of preparation. In certain embodiments the oxidizing agent comprises a basic solvent. In certain embodiments the conjugate acid of the basic solvent of the oxidizing agent has a pKa of between 5 and 8. In certain embodiments the oxidizing agent is a mixture of $I_2$, 3-picoline, water. In certain embodiments the oxidizing agent is a mixture of $I_2$, 2,6-lutidine, and water. In certain embodiments the oxidizing agent is a mixture of $I_2$, pyridine, NMI, and water. In certain embodiments the oxidizing agent is a mixture of $I_2$, isoquinoline, and water. In certain embodiments the oxidizing agent is a mixture of $I_2$, 2-picoline, and water. In certain embodiments the oxidizing agent is a mixture of $I_2$, 4-picoline, and water. In certain embodiments the oxidizing agent is a mixture of $I_2$, 3,5-lutidine, and water. In certain embodiments the oxidizing agent is a mixture of $I_2$, 2,5-lutidine, and water. In certain embodiments the oxidizing agent is a mixture of $I_2$, 3,4-lutidine, and water. In certain embodiments the oxidizing agent is a mixture of $I_2$, 2,3-lutidine, and water. In certain embodiments the oxidizing agent is a mixture of $I_2$, 2,4-lutidine, and water. In certain embodiments the oxidizing agent is a mixture of 0.05 M $I_2$ dissolved in a 9:1 volumetric ratio of 3-picoline and water. In certain embodiments the oxidizing agent is a mixture of 0.05 M $I_2$ dissolved in a 9:1 volumetric ratio of 2,6-lutidine and water. In certain embodiments the oxidizing agent is a mixture of 0.05 M $I_2$ dissolved in a 8:1:1 volumetric ratio of pyridine, NMI, and water.

In certain embodiments, the oxidizing agent is a mixture of $I_2$, a salt, pyridine, and water. In certain embodiments, the salt is a halide salt. In certain embodiments, the salt is an iodide salt. In certain embodiments, the salt is a bromide salt. In certain embodiments, the salt is a chloride or fluoride salt. In certain embodiments, the salt is selected from NaI, KI, LiI, or pyridinium iodide. In certain embodiments, the concentration of $I_2$ is 0.001 M, 0.002 M, 0.003 M, 0.004 M, 0.005 M, 0.006 M, 0.007 M, 0.008 M, 0.009 M, 0.01 M, 0.02 M, 0.03

M, 0.04 M, 0.05 M, 0.06 M, 0.07 M, 0.08 M, 0.09 M, or 0.1 M, or any range selected from two values above. In certain embodiments, the concentration of $I_2$ is 0.01-0.07 M, 0.01-0.02 M, 0.04-0.06 M, or 0.05 M. In certain embodiments, the concentration of the salt is the same as the concentration of $I_2$. In certain embodiments, the concentration of the salt is less than 90%, 80%, 70%, 60%, 50%, 40%, 30%, 20%, 10%, or 5% of concentration of the $I_2$. In certain embodiments, the concentration of the salt is 0.001 M, 0.002 M, 0.003 M, 0.004 M, 0.005 M, 0.006 M, 0.007 M, 0.008 M, 0.009 M, 0.01 M, 0.02 M, 0.03 M, 0.04 M, 0.05 M, 0.06 M, 0.07 M, 0.08 M, 0.09 M, or 0.1 M, or any range selected from two values above. In certain embodiments, the concentration of the salt is 0.001-0.05 M, 0.005-0.07 M, 0.01-0.07 M, 0.01-0.02M, 0.01-0.06 M, 0.02-0.06 M, 0.03-0.06 M, or 0.04-0.06 M. In certain embodiments, the concentration of the salt is 0.05 M. In certain embodiments, the oxidizing agent is a mixture of 0.05 M $I_2$, 0.05 M Nat in a 9:1 volumetric ratio of pyridine and water. In certain embodiments, the oxidizing agent is a mixture of 0.05 M $I_2$, 0.05 M KI, in a 9:1 volumetric ratio of pyridine and water. In certain embodiments, the oxidizing agent is a mixture of 0.05 M $I_2$, 0.05 M LiI, in a 9:1 volumetric ratio of pyridine and water.

In certain embodiments, processes described herein are useful for synthesizing oligomeric compounds comprising or consisting of oligonucleotides consisting of linked nucleosides. Oligonucleotides may be unmodified oligonucleotides or may be modified oligonucleotides. Modified oligonucleotides comprise at least one modification relative to an unmodified oligonucleotide (i.e., comprise at least one modified nucleoside (comprising a modified sugar moiety and/or a modified nucleobase) and/or at least one modified internucleoside linkage). The present disclosure provides oxidation agents for use in the synthesis of oligonucleotides having any number of modifications described herein.

I. Modifications

A. Modified Nucleosides

In certain embodiments, synthetic processes described herein are used to produce compounds comprising modified nucleosides comprising a modified sugar moiety, a modified nucleobase, or both a modified sugar moiety and a modified nucleobase. Certain such compounds are described.

1. Certain Modified Sugar Moieties

In certain embodiments, sugar moieties are non-bicyclic, modified furanosyl sugar moieties. In certain embodiments, modified sugar moieties are bicyclic or tricyclic furanosyl sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified furanosyl sugar moieties comprising one or more acyclic substituent, including but not limited to substituents at the 2', 4', and/or 5' positions. In certain embodiments, the furanosyl sugar moiety is a ribosyl sugar moiety. In certain embodiments one or more acyclic substituent of non-bicyclic modified sugar moieties is branched. Examples of 2'-substituent groups suitable for non-bicyclic modified sugar moieties include but are not limited to: 2'-F, 2'-$OCH_3$("OMe" or "O-methyl"), and 2'-$O(CH_2)_2OCH_3$ ("MOE"). In certain embodiments, 2'-substituent groups are selected from among: halo, allyl, amino, azido, SH, CN, OCN, $CF_3$, $OCF_3$, O—$C_1$-$C_{10}$ alkoxy, O—$C_1$-$C_{10}$ substituted alkoxy, O—$C_1$-$C_{10}$ alkyl, O—$C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C({=}O)$—$N(R_m)(R_n)$, where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or non-bicyclic 2'-modified nucleoside comprises a sugar moiety comprising a non-bridging 2'-substituent group selected from: F, $NH_2$, $N_3$, $OCF_3$, $OCH_3$, $O(CH_2)_3NH_2$, $CH_2CH{=}CH_2$, $OCH_2CH{=}CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C({=}O){-}N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted nucleoside or non-bicyclic 2'-modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C({=}O){-}N(H)CH_3$ ("NMA").

In certain embodiments, a 2'-substituted nucleoside or non-bicyclic 2'-modified nucleoside comprises a sugar moiety comprising a non-bridging 2'-substituent group selected from: F, $OCH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. In certain such embodiments, the furanose ring is a ribose ring. Examples of sugar moieties comprising such 4' to 2' bridging sugar substituents include but are not limited to bicyclic sugars comprising: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-$CH(CH_3)$—O-2' (referred to as "constrained ethyl" or "cEt" when in the S configuration), 4'-$CH_2$—O—$CH_2$-2', 4'-$CH_2$—N(R)-2', 4'-$CH(CH_2OCH_3)$—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-$C(CH_3)(CH_3)$—O-2' and analogs thereof (see, e.g., Seth et al., U.S. Pat. No. 8,278,283), 4$CH_2$—N($OCH_3$)-2' and analogs thereof (see, e.g., Prakash et al., U.S. Pat. No. 8,278,425), 4'-$CH_2$—O—N($CH_3$)-2' (see, e.g., Allerson et al., U.S. Pat. No. 7,696,345 and Allerson et al., U.S. Pat. No. 8,124,745), 4'-$CH_2$—C(H)($CH_3$)-2' (see, e.g., Zhou, et al., *J. Org. Chem.*, 2009, 74, 118-134), 4'-$CH_2$—C(═$CH_2$)-2' and analogs thereof (see e.g., Seth et al., U.S. Pat. No. 8,278,426), 4'-C($R_aR_b$)—N(R)—O-2', 4'-C($R_aR_b$)—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: $-[C(R_a)(R_b)]_n-$, $-[C(R_a)(R_b)]_n-O-$, $-C(R_a){=}C(R_b)-$, $-C(R_a){=}N-$, $-C({=}NR_a)-$, $-C({=}O)-$, $-C({=}S)-$, $-O-$, $-Si(R_a)_2-$, $-S({=}O)_x-$, and $-N(R_a)-$;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl ($C({=}O){-}H$), substituted acyl, CN, sulfonyl ($S({=}O)_2$-$J_1$), or sulfoxyl ($S({=}O)$-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl ($C({=}O){-}H$), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129, 8362-8379; Elayadi et al.,; Wengel eta., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356;Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

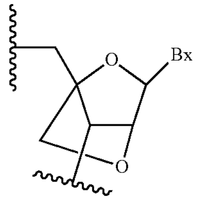

LNA (β-D-configuration)
bridge = 4'-$CH_2$-O-2'

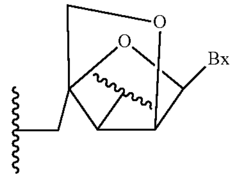

α-L-LNA (α-L-configuration)
bridge = 4'-$CH_2$-O-2'

α-L-methyleneoxy (4'-$CH_2$—O-2') or α-L-LNA bicyclic nucleosides have been incorporated into antisense oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

Nucleosides comprising modified furanosyl sugar moieties and modified furanosyl sugar moieties may be referred to by the position(s) of the substitution(s) on the sugar moiety of the nucleoside. The term "modified" following a position of the furanosyl ring, such as "2'-modified", indicates that the sugar moiety comprises the indicated modification at the 2' position and may comprise additional modifications and/or substituents. The term "substituted" following a position of the furanosyl ring, such as "2'-substituted" or "2'-4'-substituted", indicates that is the only position(s) having a substituent other than those found in unmodified sugar moieties in oligonucleotides. Accordingly, the following sugar moieties are represented by the following formulas.

In the context of a nucleoside and/or an oligonucleotide, a non-bicyclic, modified furanosyl sugar moiety is represented by formula I:

I

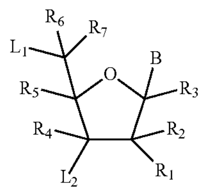

wherein B is a nucleobase; and $L_1$ and $L_2$ are each, independently, an internucleoside linkage, a terminal group, a conjugate group, or a hydroxyl group. Among the R groups, at least one of $R_{3-7}$ is not H and/or at least one of $R_1$ and $R^2$ is not H or OH. In a 2'-modified furanosyl sugar moiety, at least one of $R_1$ and $R_2$ is not H or OH and each of $R_{3-7}$ is independently selected from H or a substituent other than H. In a 4'-modified furanosyl sugar moiety, $R_5$ is not H and each of $R_{1-4,\ 6,\ 7}$ are independently selected from H and a substituent other than H; and so on for each position of the furanosyl ring. The stereochemistry is not defined unless otherwise noted.

In the context of a nucleoside and/or an oligonucleotide, a non-bicyclic, modified, substituted furanosyl sugar moiety is represented by formula I, wherein B is a nucleobase; and $L_1$ and $L_2$ are each, independently, an internucleoside linkage, a terminal group, a conjugate group, or a hydroxyl group. Among the R groups, either one (and no more than one) of $R_{3-7}$ is a substituent other than H or one of $R_1$or $R_2$ is a substituent other than H or OH. The stereochemistry is not defined unless otherwise noted. Examples of non-bicyclic, modified, substituted furanosyl sugar moieties include 2'-substituted ribosyl, 4'-substituted ribosyl, and 5'-substituted ribosyl sugar moieties, as well as substituted 2'-deoxyfuranosyl sugar moieties, such as 4'-substituted 2'-deoxyribosyl and 5'-substituted 2'-deoxyribosyl sugar moieties.

In the context of a nucleoside and/or an oligonucleotide, a 2'-substituted ribosyl sugar moiety is represented by formula II:

II

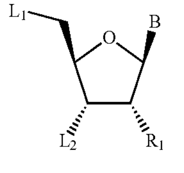

wherein B is a nucleobase; and $L_1$ and $L_2$ are each, independently, an internucleoside linkage, a terminal group, a conjugate group, or a hydroxyl group. $R_1$ is a substituent other than H or OH. The stereochemistry is defined as shown.

In the context of a nucleoside and/or an oligonucleotide, a 4'-substituted ribosyl sugar moiety is represented by formula III:

III

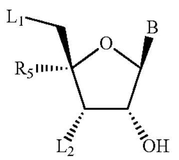

wherein B is a nucleobase; and $L_1$ and $L_2$ are each, independently, an internucleoside linkage, a terminal group, a conjugate group, or a hydroxyl group. $R_5$ is a substituent other than H. The stereochemistry is defined as shown.

In the context of a nucleoside and/or an oligonucleotide, a 5'-substituted ribosyl sugar moiety is represented by formula IV:

IV

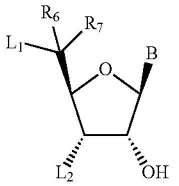

wherein B is a nucleobase; and $L_1$ and $L_2$ are each, independently, an internucleoside linkage, a terminal group, a conjugate group, or a hydroxyl group. $R_6$ or $R_7$ is a substituent other than H. The stereochemistry is defined as shown.

In the context of a nucleoside and/or an oligonucleotide, a 2'-deoxyfuranosyl sugar moiety is represented by formula V:

V

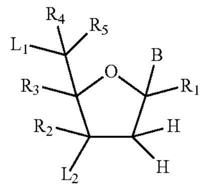

wherein B is a nucleobase; and $L_1$ and $L_2$ are each, independently, an internucleoside linkage, a terminal group, a conjugate group, or a hydroxyl group. Each of $R_{1-5}$ are independently selected from H and a non-H substituent. If all of $R_{1-5}$ are each H, the sugar moiety is an unsubstituted 2'-deoxyfuranosyl sugar moiety. The stereochemistry is not defined unless otherwise noted.

In the context of a nucleoside and/or an oligonucleotide, a 4'-substituted 2'-deoxyribosyl sugar moiety is represented by formula VI:

VI

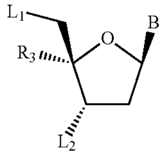

wherein B is a nucleobase; and $L_1$ and $L_2$ are each, independently, an internucleoside linkage, a terminal group, a conjugate group, or a hydroxyl group. $R_3$ is a substituent other than H. The stereochemistry is defined as shown.

In the context of a nucleoside and/or an oligonucleotide, a 5'-substituted 2'-deoxyribosyl sugar moiety is represented by formula VII:

VII

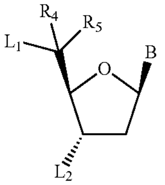

wherein B is a nucleobase; and $L_1$ and $L_2$ are each, independently, an internucleoside linkage, a terminal group, a conjugate group, or a hydroxyl group. $R_4$ or $R_5$ is a substituent other than H. The stereochemistry is defined as shown.

Unsubstituted 2'-deoxyfuranosyl sugar moieties may be unmodified (β-D-2'-deoxyribosyl) or modified. Examples of modified, unsubstituted 2'-deoxyfuranosyl sugar moieties include β-L-2'-deoxyribosyl, α-L-2'-deoxyribosyl, α-D-2'-deoxyribosyl, and β-D-xylosyl sugar moieties. For example, in the context of a nucleoside and/or an oligonucleotide, a β-L-2'-deoxyribosyl sugar moiety is represented by formula VIII:

VIII

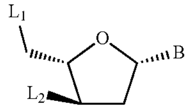

wherein B is a nucleobase; and $L_1$ and $L_2$ are each, independently, an internucleoside linkage, a terminal group, a conjugate group, or a hydroxyl group. The stereochemistry is defined as shown.

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

F-HNA

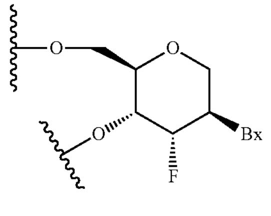

("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

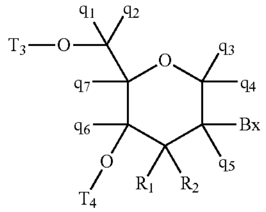

wherein, independently, for each of said modified THP nucleoside:

Bx is a nucleobase moiety;

$T_3$ and $T_4$ are each, independently, an internucleoside linkage linking the modified THP nucleoside to the remainder of an oligonucleotide or one of $T_3$ and $T_4$ is an internucleoside linkage linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

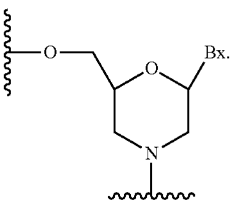

In certain embodiments, morpholinos may be modified, for example by adding or altering various substituent groups from the above morpholino structure. Such sugar surrogates are refered to herein as "modifed morpholinos."

Many other bicyclic and tricyclic sugar and sugar surrogate ring systems are known in the art that can be used in modified nucleosides.

In certain embodiments, modified nucleosides are DNA mimics. In certain embodiments, a DNA mimic is a sugar surrogate. In certain embodiments, a DNA mimic is a cycohexenyl or hexitol nucleic acid. In certain embodiments, a DNA mimic is described in FIG. 1 of Vester, et. al., "Chemically modified oligonucleotides with efficient RNase H response," *Bioorg. Med. Chem. Letters,* 2008, 18: 2296-2300, incorporated by reference herein. In certain embodiments, a DNA mimic nucleoside has a formula selected from:

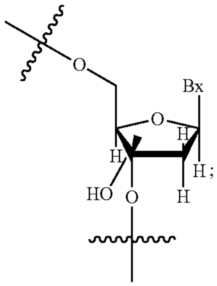

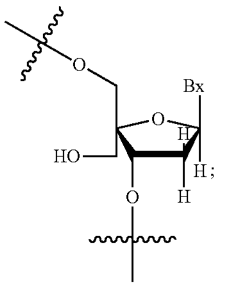

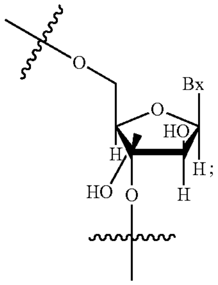

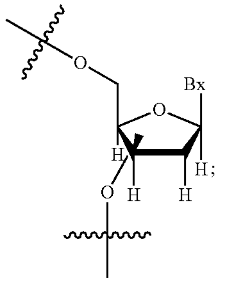

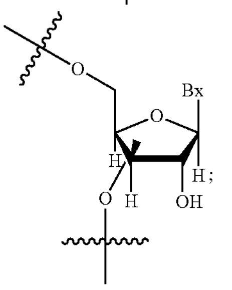

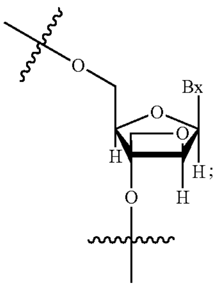

-continued

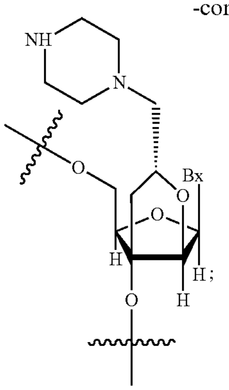

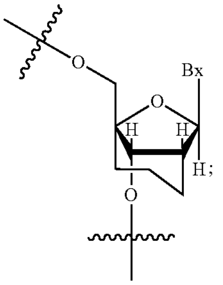

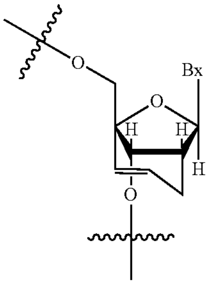

wherein Bx is a heterocyclic base moiety. In certain embodiments, a DNA mimic is α,β-constrained nucleic acid (CAN), 2',4'-carbocyclic-LNA, or 2',4'-carbocyclic-ENA. In certain embodiments, a DNA mimic has a sugar moiety selected from among: 4'-C-hydroxymethyl-2'-deoxyribosyl, 3'-C-hydroxyme thyl-2'-deoxyribosyl, 3'-C-hydroxymethyl-arabinosyl, 3'-C-2'-O-arabinosyl, 3'-C-methylene-extended-2'-deoxyxylosyl, 3'-C-methylene-extended-xyolosyl, 3'-C-2'-O-piperazino-arabinosyl. In certain embodiments, a DNA mimic has a sugar moiety selected from among: 2'-methylribosyl, 2'-S-methylribosyl, 2'-aminoribosyl, 2'-NH($CH_2$)-ribosyl, 2'-NH($CH_2$)$_2$-ribosyl, 2'-$CH_2$—F-ribosyl, 2'-$CHF_2$-ribosyl, 2'-$CF_3$-ribosyl, 2'=CF2 ribosyl, 2'-ethylribosyl, 2'-alkenylribosyl, 2'-alkynylribosyl, 2'-O-4'-C-me thyleneribosyl, 2'-cyanoarabinosyl, 2'-chloroarabinosyl, 2'-fluoroarabinosyl, 2'-bromoarabinosyl, 2'-azidoarabinosyl, 2'-methoxyarabinosyl, and 2'-arabinosyl. In certain embodiments, a DNA mimic has a sugar moiety selected from 4'-methyl-modified deoxyfuranosyl, 4'-F-deoxyfuranosyl, 4'-OMe-deoxyfuranosyl. In certain embodiments, a DNA mimic has a sugar moiety selected from among: 5'-methyl-2'-β-D-deoxyribosyl, 5'-ethyl-2'-β-D-deoxyribosyl, 5'-allyl-2'-β-D-deoxyribosyl, 2'-fluoro-β-D-arabinofuranosyl. In certain embodiments, DNA mimics are listed on page 32-33 of PCT/US00/267929 as B-form nucleotides, incorporated by reference herein in its entirety.

2. Modified Nucleobases

In certain embodiments, synthetic processes disclosed herein are useful for making oligomeric compounds having at least one modified nucleoside comprising a modified nucleobase. Modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($-C\equiv CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering,* Kroschwitz, J. I., Ed., John Wiley & Sons, 1990, 858-859; Englisch et al., *Angewandte Chemie,* International Edition, 1991, 30, 613; Sanghvi, Y. S., Chapter 15, *Antisense Research and Applications,* Crooke, S. T. and Lebleu, B., Eds., CRC Press, 1993, 273-288; and those disclosed in Chapters 6 and 15, *Antisense Drug Technology,* Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403; Manoharan et al., US2003/0175906;; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No.6,005,096.

In certain embodiments, processes described herein are useful for synthesizing compounds that comprise or consist of a modified oligonucleotide complementary to a target nucleic acid comprising one or more modified nucleobases. In certain embodiments, the modified nucleobase is 5-methylcytosine. In certain embodiments, each cytosine is a 5-methylcytosine.

B. Modified Internucleoside Linkages

In certain embodiments, processes described herein are useful for synthesizing oligomeric compounds having one or more modified internucleoside linkage. In certain embodiments, such compounds are selected over compounds having only phosphate diester internucleoside linkages because of desirable properties such as, for example, enhanced cellular uptake, enhanced affinity for target nucleic acids, and increased stability in the presence of nucleases.

The two main classes of internucleoside linkages are defined by the presence or absence of a phosphorus atom. Representative phosphorus-containing internucleoside linkages include unmodified phosphate diester internucleoside linkages, modified phosphotriesters such as THP phosphotriester and isopropyl phosphotriester, phosphonates such as methylphosphonate, isopropyl phosphonate, isobutyl phosphonate, and phosphonoacetate, phosphoramidates, and phosphorodithioate ("HS—P=S"). Representative non-phosphorus containing internucleoside linkages include but are not limited to methylenemethylimino ($-CH_2-N(CH_3)-O-CH_2-$), thiodiester, thionocarbamate ($-O-C(=O)(NH)-S-$); siloxane ($-O-SiH_2-O-$); formacetal, thioacetamido (TANA), alt-thioformacetal, glycine amide, and N,N'-dimethylhydrazine ($-CH_2-N(CH_3)-N(CH_3)-$). Modified internucleoside linkages, compared to naturally occurring phosphate linkages, can be used to alter, typically increase, nuclease resistance of the oligonucleotide. Methods of preparation of phosphorous-containing and non-phosphorous-containing internucleoside linkages are well known to those skilled in the art.

Representative internucleoside linkages having a chiral center include but are not limited to alkylphosphonates and phosphorothioate diesters. Modified oligonucleotides comprising internucleoside linkages having a chiral center can be prepared as populations of modified oligonucleotides comprising stereorandom internucleoside linkages, or as populations of modified oligonucleotides comprising phosphorothioate diester linkages in particular stereochemical configurations. In certain embodiments, populations of modified oligonucleotides comprise phosphorothioate diester internucleoside linkages wherein all of the phosphorothioate diester internucleoside linkages are stereorandom. Such modified oligonucleotides can be generated using synthetic methods that result in random selection of the stereochemical configuration of each phosphorothioate diester linkage. Nonetheless, as is well understood by those of skill in the art, each individual phosphorothioate diester of each individual oligonucleotide molecule has a defined stereoconfiguration. In certain embodiments, populations of modified oligonucleotides are enriched for modified oligonucleotides comprising one or more particular phosphorothioate diester internucleoside linkages in a particular, independently selected stereochemical configuration. In certain embodiments, the particular configuration of the particular phosphorothioate diester linkage is present in at least 65% of the molecules in the population. In certain embodiments, the particular configuration of the particular phosphorothioate diester linkage is present in at least 70% of the molecules in the population. In certain embodiments, the particular configuration of the particular phosphorothioate diester linkage is present in at least 80% of the molecules in the population. In certain embodiments, the particular configuration of the particular phosphorothioate diester linkage is present in at least 90% of the molecules in the population. In certain embodiments, the particular configuration of the particular phosphorothioate diester linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate diester in the (Sp) configuration. In certain embodiments, a population of modified oligonucleotides is enriched for modified oligonucleotides having at least one phosphorothioate diester in the (Rp) configuration. In certain embodiments, modified oligonucleotides comprising (Rp) and/or (Sp) phosphorothioate diesters comprise one or more of the following formulas, respectively, wherein "B" indicates a nucleobase:

($R_p$)

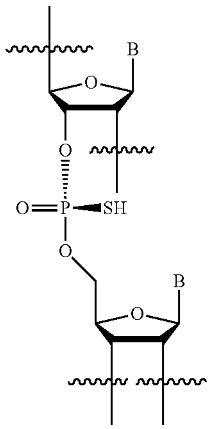

($S_p$)

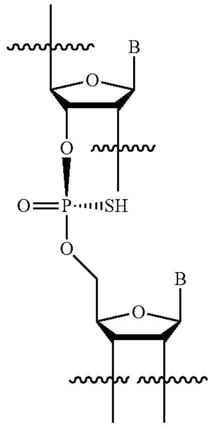

Unless otherwise indicated, chiral internucleoside linkages of modified oligonucleotides described herein can be stereorandom or in a particular stereochemical configuration. The oxidizing agents described herein are suitable for use in synthesis of oligonucleotides having one or more chirally controlled linkage.

Neutral internucleoside linkages include, without limitation, phosphotriesters, phosphonates, MMI (3'-$CH_2$—N($CH_3$)—O-5'), amide-3 (3'-$CH_2$—C(═O)—N(H)-5'), amide-4 (3'-$CH_2$—N(H)—C(═O)-5'), formacetal (3'-O—$CH_2$—O-5'), methoxypropyl, and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, synthetic processes disclosed herein result in a phosphate diester internucleoside linkage. Nevertheless, in certain embodiments, other internucleoside linkages within an oligonucleotide or oligomeric compound may be any of the linkages described above.

II. Certain Motifs

In certain embodiments, synthetic processes described herein are useful for making oligomeric compounds having any motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns or motifs of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

A. Certain Sugar Motifs

In certain embodiments, synthetic processes described herein are useful for making oligonucleotides that comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, synthetic processes described herein are useful for making modified oligonucleotides that comprise or have a uniformly modified sugar motif. An oligonucleotide comprising a uniformly modified sugar motif comprises a segment of linked nucleosides, wherein each nucleoside of the segment comprises the same modified sugar moiety. An oligonucleotide having a uniformly modified sugar motif throughout the entirety of the oligonucleotide comprises only nucleosides comprising the same modified sugar moiety. For example, each nucleoside of a 2'-MOE uniformly modified oligonucleotide comprises a 2'-MOE modified sugar moiety. An oligonucleotide comprising or having a uniformly modified sugar motif can have any nucleobase sequence and any internucleoside linkage motif.

B. Certain Nucleobase Motifs

In certain embodiments, synthetic processes described herein are useful for making oligonucleotides that comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

C. Certain Internucleoside Linkage Motifs

The synthetic processes described herein are particularly useful in synthesizing oligonucleotides or oligomeric compounds having particular linkage motifs. In certain embodiments, oligonucleotides comprise modified and/or unmodified internucleoside linkages arranged along the oligonucleotide or region thereof in a defined pattern or motif. In certain embodiments, each internucleoside linkage of a modified oligonucleotide is a phosphorothioate diester internucleoside linkage (P═S) and the compound includes a conjugate group comprising at least one phosphate diester. In certain embodiments, each internucleoside linkage of a modified oligonucleotide is independently selected from a phosphorothioate diester internucleoside linkage and phosphate diester internucleoside linkage. In certain embodiments, each phosphorothioate diester internucleoside linkage is independently selected from a stereorandom phosphorothioate diester, a (Sp) phosphorothioate diester, and a (Rp) phosphorothioate diester. In certain embodiments, the terminal internucleoside linkages are modified. In certain embodiments, the internucleoside linkage motif comprises at least one phosphate diester internucleoside linkage in at least one of the 5'-region and the 3'-region, wherein the at least one phosphate diester linkage is not a terminal internucleoside linkage, and the remaining internucleoside linkages are phosphorothioate diester internucleoside linkages. In certain such embodiments, all of the phosphorothioate diester linkages are stereorandom. In certain embodiments, populations of modified oligonucleotides are enriched for modified oligonucleotides comprising such internucleoside linkage motifs.

In certain embodiments, oligonucleotides comprise a region having an alternating internucleoside linkage motif. In certain embodiments, oligonucleotides comprise a region of uniformly modified internucleoside linkages. In certain such embodiments, the internucleoside linkages are phosphorothioate diester internucleoside linkages. In certain embodiments, all of the internucleoside linkages of the oligonucleotide are phosphorothioate diester internucleoside linkages. In certain embodiments, each internucleoside linkage of the oligonucleotide is selected from phosphate diester or phosphate and phosphorothioate diester and at least one internucleoside linkage is a phosphorothioate diester and at least one internucleoside linkage is a phosphate diester.

In certain embodiments, the oligonucleotide comprises at least 6 phosphorothioate diester internucleoside linkages. In certain embodiments, the oligonucleotide comprises at least 8 phosphorothioate diester internucleoside linkages. In certain embodiments, the oligonucleotide comprises at least 10 phosphorothioate diester internucleoside linkages. In certain embodiments, the oligonucleotide comprises at least one block of at least 6 consecutive phosphorothioate diester internucleoside linkages. In certain embodiments, the oligonucleotide comprises at least one block of at least 8 consecutive phosphorothioate diester internucleoside linkages. In certain embodiments, the oligonucleotide comprises at least one block of at least 10 consecutive phosphorothioate diester internucleoside linkages. In certain embodiments, the oligonucleotide comprises at least block of at least one 12 consecutive phosphorothioate diester internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, it is desirable to arrange the number of phosphorothioate diester internucleoside linkages and phosphate diester internucleoside linkages to maintain nuclease resistance. In certain embodiments, it is desirable to arrange the number and position of phosphorothioate diester internucleoside linkages and the number and position of phosphate diester internucleoside linkages to maintain nuclease resistance. In certain embodiments, the number of phosphorothioate diester internucleoside linkages may be decreased and the number of phosphate diester internucleoside linkages may be increased. In certain embodiments, the number of phosphorothioate diester internucleoside linkages may be decreased and the number of phosphate diester internucleoside linkages may be increased while still maintaining nuclease resistance. In certain embodiments it is desirable to decrease the number of phosphorothioate diester internucleoside linkages while retaining nuclease resistance. In certain embodiments it is desirable to increase the number of phosphate diester internucleoside linkages while retaining nuclease resistance.

III. Certain Modified Oligonucleotides

In certain embodiments, oligonucleotides synthesized using processes described herein consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

In certain embodiments oligonucleotides synthesized using processes described herein have a nucleobase sequence that is complementary to a second oligonucleotide or an identified reference nucleic acid, such as a target nucleic acid. In certain embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 70%, at least 80%, at least 90%, at least 95%, or 100% complementary to the second oligonucleotide or nucleic acid, such as a target nucleic acid.

IV. Certain Conjugated Compounds

In certain embodiments, the oligomeric compounds synthesized using processes described herein comprise or consist of an oligonucleotide (modified or unmodified) and optionally one or more conjugate groups and/or terminal groups. Conjugate groups consist of one or more conjugate moiety and a conjugate linker that links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides synthesized using processes described herein are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide.

Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic, a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, i, 923-937), a tocopherol group (Nishina et al., *Molecular Therapy Nucleic Acids,* 2015, 4, e220; doi:10.1038/mtna.2014.72 and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, a conjugate linker is a single chemical bond (i.e. conjugate moiety is attached to an oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the synthetic processes described herein are useful for making conjugate linkers comprising one or more phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to oligomeric compounds, such as the oligonucleotides provided herein. In general, a bifunctional linking moiety comprises at least two functional groups. One of the functional groups is selected to bind to a particular site on an oligomeric compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphate diester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, an oligomeric compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the compound has been taken up, it is desirable that the conjugate group be cleaved to release the unconjugated oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphate diester, a phosphate ester, a carbamate, or a disulfide. In certain embodiments, a cleavable bond is one or both of the esters of a phosphate diester. In certain embodiments, a cleavable moiety comprises a phosphate or phosphate diester. In certain embodiments, the cleavable moiety is a phosphate linkage between an oligonucleotide and a conjugate moiety or conjugate group. In certain embodiments, the synthetic processes described herein are useful for making phosphate diester cleavable moieties.

In certain embodiments, a cleavable moiety comprises or consists of one or more linker-nucleosides. In certain such embodiments, one or more linker-nucleosides are linked to one another and/or to the remainder of the oligomeric compound through cleavable bonds. In certain embodiments, such cleavable bonds are unmodified phosphate diester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate diester linkage. In certain such embodiments, the cleavable moiety is 2'-deoxyadenosine.

3. Certain Cell-Targeting Conjugate Moieties

In certain embodiments, a conjugate group comprises a cell-targeting conjugate moiety. In certain embodiments, a conjugate group has the general formula:

[Ligand-Tether]$_n$-[Branching group]$_m$-[Conjugate Linker]$_j$-[Cleavable Moiety]$_k$—

Cell-targeting moiety wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphate diester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphate diester, ether, amino, oxo, and amide, in any combination. In certain embodiments, each tether is a linear aliphatic group comprising one or more groups selected from alkyl, ether, amino, oxo, and amid, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphate diester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian lung cell.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," *Bioconjugate Chemistry,* 2003, 14, 18-29, or Rensen et al., "Design and Synthesis of Novel N-Acetylgalactosamine-Terminated Glycolipids for Targeting of Lipoproteins to the Hepatic Asiaglycoprotein Receptor," *J Med. Chem.* 2004, 47, 5798-5808, which are incorporated herein by reference in their entirety). In certain such embodiments, each ligand is an amino sugar or a thio sugar. For example, amino sugars may be selected from any number of compounds known in the art, such as sialic acid, α-D-galactosamine, β-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycolyl-α-neuraminic acid. For example, thio sugars may be selected from 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, oligomeric compounds synthesized using processes described herein comprise a conjugate group found in any of the following references: Lee, *Carbohydr Res,* 1978, 67, 509-514; Connolly et al., *J Biol Chem,* 1982, 257, 939-945; Pavia et al., *Int J Pep Protein Res,* 1983, 22, 539-548; Lee et al., *Biochem,* 1984, 23, 4255-4261; Lee et al., *Glycoconjugate J,* 1987, 4, 317-328; Toyokuni et al., *Tetrahedron Lett,* 1990, 31, 2673-2676; Biessen et al., *J Med Chem,* 1995, 38, 1538-1546; Valentijn et al., *Tetrahedron,* 1997, 53, 759-770; Kim et al., *Tetrahedron Lett,* 1997, 38, 3487-3490; Lee et al., *Bioconjug Chem,* 1997, 8, 762-765; Kato et al., *Glycobiol,* 2001, 11, 821-829; Rensen et al., *J Biol Chem,* 2001, 276, 37577-37584; Lee et al., *Methods Enzymol,* 2003, 362, 38-43; Westerlind et al.,*Glycoconj J,* 2004, 21, 227-241; Lee et al., *Bioorg Med Chem Lett,* 2006, 16(19), 5132-5135; Maierhofer et al., *Bioorg Med Chem,* 2007, 15, 7661-7676; Khorev et al., *Bioorg Med Chem,* 2008, 16, 5216-5231; Lee et al., *Bioorg Med Chem,* 2011, 19, 2494-2500; Kornilova et al., Analyt Biochem, 2012, 425, 43-46; Pujol et al., *Angew Chemie Int Ed Engl,* 2012, 51, 7445-7448; Biessen et al., *J Med Chem,* 1995, 38, 1846-1852; Sliedregt et al., *J Med Chem,* 1999, 42, 609-618; Rensen et al., *J Med Chem,* 2004, 47, 5798-5808; Rensen et al., *Arterioscler Thromb Vasc Biol,* 2006, 26, 169-175; van Rossenberg et al., *Gene Ther,* 2004, 11, 457-464; Sato et al.,

*J Am Chem Soc,* 2004, 126, 14013-14022; Lee et al., *J Org Chem,* 2012, 77, 7564-7571; Biessen et al., *FASEB J,* 2000, 14, 1784-1792; Rajur et al., *Bioconjug Chem,* 1997, 8, 935-940; Duff et al., Methods Enzymol, 2000, 313, 297-321; Maier et al., Bioconjug Chem, 2003, 14, 18-29; Jayaprakash et al., *Org Lett,* 2010, 12, 5410-5413; Manoharan, *Antisense Nucleic Acid Drug Dev,* 2002, 12, 103-128; Merwin et al., *Bioconjug Chem,* 1994, 5, 612-620; Tomiya et al., Bioorg Med Chem, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132.

Target Nucleic Acids

In certain embodiments, oligonucleotides synthesized using processes described herein comprise or consist of an oligonucleotide that is complementary to a target nucleic acid. In certain embodiments, the target nucleic acid is an endogenous RNA molecule. In certain embodiments, the target nucleic acid encodes a protein. In certain such embodiments, the target nucleic acid is an mRNA. In certain embodiments, an oligonucleotide is complementary to both a pre-mRNA and corresponding mRNA but only the mRNA is the target nucleic acid due to an absence of antisense activity upon hybridization to the pre-mRNA. In certain embodiments, an oligonucleotide is complementary to an exon-exon junction of a target mRNA and is not complementary to the corresponding pre-mRNA.

Compound Isomers

Certain oligonucleotides synthesized using processes described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms. All tautomeric forms of the compounds provided herein are included unless otherwise indicated.

The oligonucleotides synthesized using processes described herein include variations in which one or more atoms are replaced with a non-radioactive isotope or radioactive isotope of the indicated element. For example, compounds herein that comprise hydrogen atoms encompass all possible deuterium substitutions for each of the $^{1}H$ hydrogen atoms. Isotopic substitutions encompassed by the compounds herein include but are not limited to: $^{2}H$ or $^{3}H$ in place of $^{1}H$, $^{13}C$ or $^{14}C$ in place of $^{12}C$, $^{15}N$ in place of $^{14}N$, $^{17}O$ or $^{18}O$ in place of $^{16}O$, and $^{33}S$, $^{34}S$, $^{35}S$, or $^{36}S$ in place of $^{32}S$. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

Non-Limiting Disclosure and Incorporation by Reference

Although the sequence listing accompanying this filing identifies each sequence as either “RNA” or “DNA” as required, in reality, those sequences may be modified with any combination of chemical modifications. One of skill in the art will readily appreciate that such designation as “RNA” or “DNA” to describe modified oligonucleotides is, in certain instances, arbitrary. For example, an oligonucleotide comprising a nucleoside comprising a 2'-OH sugar moiety and a thymine nucleobase could be described as a DNA having an RNA sugar, or as an RNA having a DNA nucleobase.

Accordingly, nucleic acid sequences provided herein, including, but not limited to those in the sequence listing, are intended to encompass nucleic acids containing any combination of unmodified or modified RNA and/or DNA, including, but not limited to such nucleic acids having modified nucleobases. By way of further example and without limitation, an oligonucleotide having the nucleobase sequence “ATCGATCG” encompasses any oligonucleotides having such nucleobase sequence, whether modified or unmodified, including, but not limited to, such compounds comprising RNA bases, such as those having sequence “AUCGAUCG” and those having some DNA bases and some RNA bases such as “AUCGATCG” and compounds having other modified nucleobases, such as “AT$^{m}$CGAUCG,” wherein $^{m}$C indicates a cytosine base comprising a methyl group at the 5-position.

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Oligonucleotide Targeted to Human TTR

Transthyretin (TTR) (also known as prealbumin, hyperthytoxinemia, dysprealbuminemic, thyroxine; senile systemic amyloidosis, amyloid polyneuropathy, amyloidosis I, PALB; dystransthyretinemic, $HST_{2651}$; TBPA; dysprealbuminemic euthyroidal hyperthyroxinemia) is a serum/plasma and cerebrospinal fluid protein responsible for the transport of thyroxine and retinol (Sakaki et al, Mol Biol Med. 1989, 6:161-8). Structurally, TTR is a homotetramer; point mutations and misfolding of the protein leads to deposition of amyloid fibrils and is associated with disorders, such as senile systemic amyloidosis (SSA), familial amyloid polyneuropathy (FAP), and familial amyloid cardiopathy (FAC).

The oligonucleotide in Table 1 below was designed to be complementary to mutant TTR and when administered to a subject in need thereof reduce expression of mutant TTR to ameliorate one or more symptoms of TTR amyloidosis. As illustrated by the Table 1 below, Compound No. 682884 contains both phosphate diester and phosphorothioate diester linkages, including a phosphate diester linkage at the 5' most nucleoside linked to the GalNAc$_3$-7$_{a\text{-}o}$ conjugate.

The synthesis of Compound No. 682884 requires the addition of 20 nucleotides to a universal linker-loaded solid support. After the addition of the nucleotides, an aminohexyl linker is added to the to the 5'-most nucleotide. Accordingly, there are 20 separate reaction cycles to add each subsequent nucleotide and one additional reaction cycle to add the aminohexyl linker. GalNAc$_3$-7 is added to the fully assembled aminohexyl-derivatized oligonucleotide in a separate solution-phase step. With the mix of phosphorothioate diester linkages and phosphate diester linkages, there are a total of 7 oxidation cycles (the six phosphate diester internucleotide linkages and the final phosphate diester linkage between the 5'-most nucleotide and the aminohexyl linker).

TABLE 1

Oligonucleotide targeting human TTR

| | Sequence 5' to 3' | Linkages | SEQ ID No. |
|---|---|---|---|
| 682884 | **GalNAc$_3$-7$_{a\text{-}o'}$** $T_{es}{}^{m}C_{eo}T_{eo}T_{eo}G_{eo}G_{ds}T_{ds}T_{ds}A_{ds}{}^{m}C_{ds}A_{ds}$ $T_{ds}G_{ds}A_{ds}A_{ds}A_{eo}T_{eo}{}^{m}C_{es}{}^{m}C_{es}{}^{m}C_{e}$ | PS/PO | 1 |

In the table above, capital letters indicate the nucleobase for each nucleoside and $^{m}$C indicates a 5-methyl cytosine. Subscripts: "e" indicates a 2'-MOE modified nucleoside; "d" indicates a β-D-2'-deoxyribonucleoside; "s" indicates a phosphorothioate diester internucleoside linkage (PS); "o" indicates a phosphate diester internucleoside linkage (PO). Conjugate groups are in bold.

The experiments described herein describe the synthesis of the aminohexyl precursor of Compound No. 682884, which has a protected aminohexyl linker joined to the 5' nucleoside via a phosphate diester linkage, as shown below:

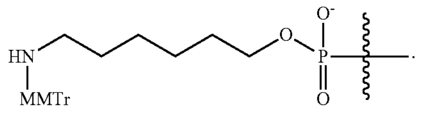

The solution-phase step of the addition of the 5'-GalNAc is independent of the solid-phase synthesis steps improved on herein.

The structure of GalNAc$_3$-7 (GalNAc$_3$-7$_{ao}$) is shown below:

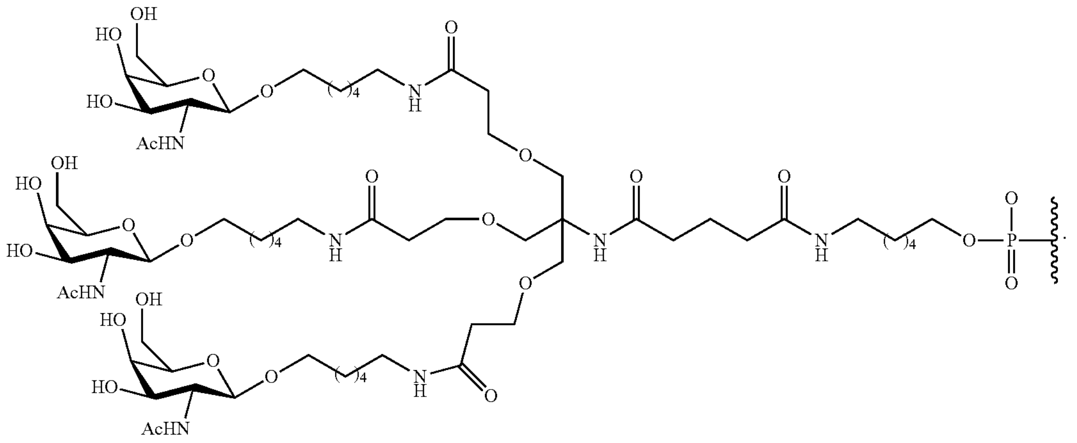

Example 2: Preparation of Different Oxidation Reagents and Identification of the (P═O)$_1$ Impurity Four different oxidation agents were made and are listed in Table 2 below. For each oxidation agent, each reagent was added to a tank and the resulting solutions were stirred at 350 RPM for approximately 17 hours.

Oxidizer 1 is the standard oxidizing reagent used for the synthesis of oligonucleotides having one or more phosphate diester bonds.

TABLE 2

Oxidizing Agents

| Solution Name | $I_2$ Molarity | Solvent Mix |
|---|---|---|
| Oxidizer 1 | 0.05 | 9:1 pyridine:$H_2O$ (v/v) |
| Oxidizer 2 | | 9:1 3-picoline:$H_2O$ (v/v) |
| Oxidizer 3 | | 9:1 2,6-lutidine:$H_2O$ (v/v) |
| Oxidizer 4 | | 8:1:1 pyridine:NMI:$H_2O$ (v/v/v) |

NMI is N-methyl imidazole.

Example 3: Synthesis of Compound 682884 Precursor with Oxidizer 1 and Oxidizer 2 after 20 Hours of Aging The aminohexyl precursor of Compound No. 682884 was synthesized using Oxidizer 1 aged for 20 hours, Oxidizer 2 aged for 20 hours, and Aged Oxidizer 1 that had been aged for 667 days. The $(P{=}O)_1$ impurity was detected by ion-pair HPLC-mass spectrometry (IP-HPLC-MS), using an Agilent single quadrupole mass spectrometer. The $(P{=}O)_1$ impurity occurs when the oxidizing reagent converts a phosphorothioate triester linkage that has already been incorporated into the oligonucleotide into a phosphate triester or phosphate diester linkage. This results in an impurity that has an additional phosphate diester linkage in place of a phosphorothioate diester linkage. Accordingly, compounds with the $(P{=}O)_1$ impurity will have a different mass compared to compounds without the $(P{=}O)_1$ impurity. The percentage of the $(P{=}O)_1$ impurity is shown in the table below.

TABLE 3

| Oxidizing Reagent | Aging Time | $(P{=}O)_1$ impurity (%) |
|---|---|---|
| Aged Oxidizer 1 | 667 days | 1.0 |
| Oxidizer 1 | 20 hours | 18.0 |
| Oxidizer 2 | 20 hours | 11.9 |

This example demonstrates that when used to synthesize the aminohexyl precursor of Compound No. 682884, Oxidizer 1 had a far higher percentage of the $(P{=}O)_1$ impurity compared to Aged Oxidizer 1. Oxidizer 2 had lower $(P{=}O)_1$ impurity compared to Oxidizer 1.

Example 4: Synthesis of Compound 682884 Precursor with Oxidizer 3 and Oxidizer 4 after 20 Hours of Aging The aminohexyl precursor of Compound No. 682884 was synthesized using Oxidizer 3 aged for 20 hours, Oxidizer 4 aged for 20 hours, and Aged Oxidizer 1 that had been aged for 674 days. The percentage of the $(P{=}O)_1$ impurity is shown in the table below.

TABLE 4

| Oxidizing Reagent | Aging Time | $(P{=}O)_1$ impurity (%) |
|---|---|---|
| Aged Oxidizer 1 | 674 days | 1.1 |
| Oxidizer 3 | 20 hours | 1.4 |
| Oxidizer 4 | 20 hours | 2.5 |

This example demonstrates that when used to synthesize the aminohexyl precursor of Compound No. 682884, Aged Oxidizer 1, Oxidizer 3, and Oxidizer 4 all produced the aminohexyl precursor of Compound No. 682884 with a very low percentage of the $(P{=}O)_1$ impurity. Oxidizer 3 and Oxidizer 4 produced the aminohexyl precursor of Compound No. 682884 with near identical levels of the $(P{=}O)_1$ impurity as was produced using Aged Oxidizer 1, and Oxidizer 3 and Oxidizer 4 could be used within a day of being made.

Example 5: Synthesis of Compound 682884 Precursor with Oxidizer 1 and Oxidizer 2 after 14 Days of Aging The aminohexyl precursor of Compound No. 682884 was synthesized using Oxidizer 1 aged for 14 days, Oxidizer 2 aged for 14 days, and Aged Oxidizer 1 that had been aged for 681 days. The percentage of the $(P{=}O)_1$ impurity is shown in the table below.

TABLE 5

| Oxidizing Reagent | Aging Time | $(P{=}O)_1$ impurity (%) |
|---|---|---|
| Aged Oxidizer 1 | 681 days | 1.1 |
| Oxidizer 1 | 14 days | 15.0 |
| Oxidizer 2 | 14 days | 1.2 |

This example demonstrates that when used to synthesize the aminohexyl precursor of Compound No. 682884, Oxidizer 1 had a far higher percentage of the $(P{=}O)_1$ impurity compared to Aged Oxidizer 1. After 14 days of aging, Oxidizer 2 had a comparable percentage of the $(P{=}O)_1$ impurity compared to Aged Oxidizer 1. Accordingly, Oxidizer 2 can be used to produce low percentages of the $(P{=}O)_1$ impurity during oligonucleotide synthesis after only 14 days of aging. For comparison, Aged Oxidizer 1 would have to age for 50 or more days to produce the same level of $(P{=}O)_1$ impurity as is produced by 14-day old Oxidizer 2.

Example 6: Synthesis of Compound 682884 Precursor with Oxidizer 3 and Oxidizer 4 after 14 Days of Aging The aminohexyl precursor of Compound No. 682884 was synthesized using Oxidizer 3 aged for 14 days, Oxidizer 4 aged for 14 days, and Aged Oxidizer 1 that had been aged for 688 days. The percentage of the $(P{=}O)_1$ impurity is shown in the table below. Incomplete oxidation can lead to the formation of the DMTr-C phosphonate impurity, which has a mass of n+286 amu.

TABLE 6

| Oxidizing Reagent | Aging Time | $(P{=}O)_1$ impurity (%) | Incomplete oxidation n + 286 amu impurity (%) |
|---|---|---|---|
| Aged Oxidizer 1 | 688 days | 1.7 | N/A |
| Oxidizer 3 | 14 days | 2.1 | 25.3 |
| Oxidizer 4 | 14 days | 1.9 | N/A |

This example demonstrates that when used to synthesize the aminohexyl precursor of Compound No. 682884, Aged Oxidizer 1, 14 day old Oxidizer 3, and 14 day old Oxidizer 4 each produced the aminohexyl precursor of Compound No. 682884 with comparable percentages of the $(P{=}O)_1$ impurity compared to Aged Oxidizer 1. Incomplete oxidation (n+286 amu) is observed for Oxidizer 3.

Example 7: Synthesis of Compound 682884 Precursor with Oxidizer 1 and Oxidizer 2 after 28 or 56 Days of Aging The aminohexyl precursor of Compound No. 682884 was synthesized using Oxidizer 1 aged for 28 days, Oxidizer 2 aged for 28 or 56 days, and Aged Oxidizer 1 that had been aged for 695 days. The percentage of the $(P{=}O)_1$ impurity is shown in the table below.

TABLE 7

| Oxidizing Reagent | Aging Time | $(P{=}O)_1$ impurity (%) | Incomplete oxidation n + 286 amu impurity (%) |
|---|---|---|---|
| Aged Oxidizer 1 | 695 days | 1.2 | Not detected |
| Oxidizer 1 | 28 days | 11.9 | N/A |
| Oxidizer 2 | 28 days | 1.0 | N/A |
| Oxidizer 2 | 56 days | N/A | 1.2 |

This example demonstrates that when used to synthesize the aminohexyl precursor of Compound No. 682884, Aged Oxidizer 1 and 28 day old Oxidizer 2 each produced the aminohexyl precursor of Compound No. 682884 with comparable percentages of the $(P{=}O)_1$ impurity. 28 day old Oxidizer 1 produced much higher levels of the $(P{=}O)_1$ impurity compared to 28 day old Oxidizer 2 and 695 day old Aged Oxidizer 1.

Example 8: Synthesis of Compound 682884 Precursor with Oxidizer 3 and Oxidizer 4 after 28 Days of Aging The aminohexyl precursor of Compound No. 682884 was synthesized using Oxidizer 3 aged for 28 days, Oxidizer 4 aged for 28 days, and Aged Oxidizer 1 that had been aged for 702 days. The percentage of the $(P{=}O)_1$ impurity is shown in the table below.

TABLE 8

| Oxidizing Reagent | Aging Time | $(P{=}O)_1$ impurity (%) | Incomplete oxidation n + 286 amu impurity (%) |
|---|---|---|---|
| Aged Oxidizer 1 | 702 days | 1.1 | Not detected |
| Oxidizer 3 | 28 days | NA | N/A |
| Oxidizer 4 | 28 days | 1.2 | 1.5 |

This example demonstrates that when used to synthesize the aminohexyl precursor of Compound No. 682884, Aged Oxidizer 1, and 28 day old Oxidizer 4 each produced the aminohexyl precursor of Compound No. 682884 with similar levels of the $(P{=}O)_1$ impurity. No data is available for Oxidizer 3, as not enough of the aminohexyl precursor of Compound No. 682884 was synthesized with 28 day old Oxidizer 3 to measure its purity profile.

Example 9: Synthesis of Compound 682884 Precursor with Oxidizer 1 Plus NaI (Oxizider 5)

A solution of 9:1 pyridine:H2O (v/v) with 0.05 M $I_2$ was prepared and stirred for 1 hour at 300 rpm. 0.05 M NaI was added to the solution and the solution was stirred for 15 minutes at 300rpm to create Oxidizer 5 (0.05M NaI, 0.05M $I_2$, 9:1 pyridine:H2O (v/v)). Synthesis of the aminohexyl precursor of Compound No. 682884 was carried out as described above using the freshly-prepared oxidizer solution or the aged solution of Oxidizer 1 described above. Contact time of the oxidation solution was 4.7 minutes for each oxidation cycle.

TABLE 9

| Oxidizing Reagent | Aging Time | $(P{=}O)_1$ impurity (%) | Incomplete oxidation n + 286 amu impurity (%) |
|---|---|---|---|
| Aged Oxidizer 1 | >700 days | 1.3 | Not detected |
| Oxidizer 5 | 1.25 hours | 1.6 | Not detected |
| Oxidizer 5 | 1 day | 1.8 | Not detected |
| Oxidizer 5 | 2 days | 1.5 | Not detected |
| Oxidizer 5 | 7 days | 1.6 | Not detected |
| Oxidizer 5 | 140 days | 1.2 | Not detected |

This example demonstrates that when used to synthesize the aminohexyl precursor of Compound No. 682884, Aged Oxidizer 1 and freshly prepared Oxidizer 5 each produced the aminohexyl precursor of Compound No. 682884 with similar levels of the $(P{=}O)_1$ impurity. Additionally, incomplete oxidation (n+286 amu) is not observed for either Aged Oxidizer 1 or Oxidizer 5 at any age tested.

Example 10: Synthesis of Compound 682884 Precursor with Aged Oxidizer 4

Synthesis of the aminohexyl precursor of Compound No. 682884 was carried out as described above using freshly prepared or aged Oxidizer 4 and compared to the aged solution of Oxidizer 1 described above. Contact time of the oxidation solution was 4.7 minutes for each oxidation cycle. In a separate experiment, twice as much of the aged Oxidizer 4 was added. Results are presented in the table below.

TABLE 10

| v | Oxidizing Reagent amount (relative to standard conditions) | Aging Time | $(P{=}O)_1$ impurity (%) | Incomplete oxidation n + 286 amu impurity (%) |
|---|---|---|---|---|
| Aged Oxidizer 1 | 1x | >700 days | 1.1 | None detected |
| Oxidizer 4 | 1x | 1.25 hours | 1.6 | No data |
| Oxidizer 4 | 1x | 35 days | 1.2 | 1.7 |
| Oxidizer 4 | 2x | 36 days | 1.4 | None detected |

This example demonstrates that when used to synthesize the aminohexyl precursor of Compound No. 682884, Aged Oxidizer 1 and freshly prepared and aged Oxidizer 4 each produced the aminohexyl precursor of Compound No. 682884 with similar levels of the $(P{=}O)_1$ impurity. This example further demonstrates that incomplete oxidation is observed with aged oxidizer 4, but complete oxidation is observed if twice as much oxidizer solution is used.

Example 11: Synthesis of Compound 682884 Precursor with Oxidizer 1 Plus NaI (Oxizider 5)

A solution of 9:1 pyridine:H2O (v/v) with 0.05 M $I_2$ was prepared and stirred for 1 hour at 300 rpm. 0.05 M KI or LiI was added to the solution and the solution was stirred for 15 minutes at 300 rpm to create Oxidizer 6 (0.05M KI, 0.05M $I_2$, 9:1 pyridine:H2O (v/v)) or Oxidizer 7 (0.05M LiI, 0.05M $I_2$, 9:1 pyridine:H2O (v/v)). Synthesis of the aminohexyl precursor of Compound No. 682884 was carried out as described above using the freshly-prepared oxidizer solution or the aged solution of Oxidizer 1 described above. Contact time of the oxidation solution was 4.7 minutes for each oxidation cycle.

TABLE 11

| Oxidizing Reagent | Iodide salt added | Aging Time | $(P{=}O)_1$ impurity (%) | Incomplete oxidation n + 286 amu impurity |
|---|---|---|---|---|
| Aged Oxidizer 1 | N/A | >700 days | 1.3 | Not detected |
| Oxidizer 5 | 0.05M NaI | 1.25 hours | 1.6 | Not detected |
| Oxidizer 6 | 0.05M KI | 1.25 hours | 1.7 | Not detected |
| Oxidizer 7 | 0.05M LiI | 1.25 hours | 1.7 | Not detected |

This example demonstrates that when used to synthesize the aminohexyl precursor of Compound No. 682884, Aged Oxidizer 1 and freshly prepared Oxidizers 5, 6, and 7 each produced the aminohexyl precursor of Compound No. 682884 with similar levels of the $(P{=}O)_1$ impurity.

What is claimed:

1. A process for synthesizing an oligomeric compound comprising an oligonucleotide, comprising contacting a first oligonucleotide intermediate having a phosphite triester linkage with an oxidizing agent to form a second oligonucleotide intermediate having a phosphate triester linkage; wherein the oxidizing agent consists of a mixture of 12, a halide salt, pyridine, and water, and wherein the concentration of $I_2$ is 0.05 M and the concentration of the halide salt is 0.05 M; wherein the halide salt is selected from NaI, KI, or LiI.

2. The process of claim 1, wherein the oxidizing agent consists of a mixture of $I_2$, a halide salt, and a 9:1 volumetric ratio of pyridine and water.

3. The process of claim 1, wherein the oligonucleotide intermediates are attached to a solid support.

4. The process of claim 1, wherein at least 4 internucleoside linkages of the oligonucleotide are phosphorothioate diester internucleoside linkages.

5. The process of claim 1, wherein each internucleoside linkage of the oligonucleotide is either a phosphorothioate diester internucleoside linkage or a phosphate diester internucleoside linkage.

6. The process of claim 1, wherein the oligomeric compound further comprises a conjugate group.

7. The process of claim 6, wherein the conjugate group comprises one or more N-acetyl galactosamine moieties.

8. The process of claim 7, wherein the conjugate group comprises Formula (V):

(V)

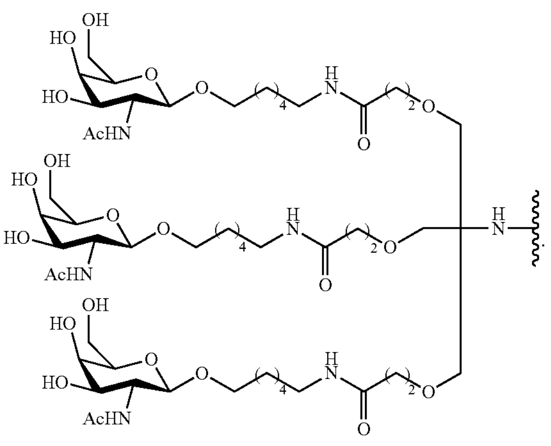

9. The process of claim 1, wherein the oligonucleotide consists of 5-40 linked nucleosides.

10. The process of claim 1, wherein the oligonucleotide consists of at least 13 linked nucleosides.

11. The process of claim 1, wherein the second oligonucleotide intermediate undergoes one or more further reactions.

12. The process of claim 11, wherein the second oligonucleotide intermediate undergoes multiple further reactions to yield an oligomeric compound comprising an oligonucleotide.

13. The process of claim 1, wherein the process results in an oligonucleotide product having less than 2%, 3%, 4%, or 5% of the $(P{=}O)_1$ impurity.

* * * * *

SEQUENCE LISTING

<160> NUMBER OF SEQ ID NOS: 1

<210> SEQ ID NO 1
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 1
tcttggttac atgaaatccc 20